United States Patent
Stefansen et al.

(10) Patent No.: US 10,799,634 B2
(45) Date of Patent: Oct. 13, 2020

(54) METHOD OF MANUFACTURING ONE OF A RANGE OF AUTOINJECTORS

(71) Applicant: Novo Nordisk A/S, Bagsvaerd (DK)

(72) Inventors: Mads Schenstroem Stefansen, Copenhagen (DK); Soeren Kjellerup Hansen, Fjenneslev (DK); Klaus Bendix, Vanloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 302 days.

(21) Appl. No.: 15/524,069

(22) PCT Filed: Nov. 12, 2015

(86) PCT No.: PCT/EP2015/076466
§ 371 (c)(1),
(2) Date: May 3, 2017

(87) PCT Pub. No.: WO2016/075254
PCT Pub. Date: May 19, 2016

(65) Prior Publication Data
US 2017/0312435 A1    Nov. 2, 2017

(30) Foreign Application Priority Data

Nov. 12, 2014  (EP) .................................. 14192895

(51) Int. Cl.
*A61M 5/20* (2006.01)
*A61M 5/315* (2006.01)
(Continued)

(52) U.S. Cl.
CPC ............ *A61M 5/2033* (2013.01); *A61M 5/24* (2013.01); *A61M 5/31541* (2013.01);
(Continued)

(58) Field of Classification Search
CPC .. A61M 5/32; A61M 5/2033; A61M 5/31541; A61M 5/3245; A61M 5/24;
(Continued)

(56) References Cited

U.S. PATENT DOCUMENTS 4,031,893 A    6/1977   Caplan et al.
5,085,640 A *  2/1992   Gibbs .................... A61B 5/154
                                                       144/145.1
(Continued)

FOREIGN PATENT DOCUMENTS

AT      409456 B     8/2002
CN      1688355 A    10/2005
(Continued)

*Primary Examiner* — Lee A Holly
(74) *Attorney, Agent, or Firm* — Wesley Nicolas

(57) ABSTRACT

A method of manufacturing one of a range of autoinjectors having cartridges (600, 600', 600") with different preset fill volumes, the method comprising the steps of: a) providing a front body assembly (100b, 100c, 100c', 100c"), b) providing a cartridge (600, 600', 600") of given fill volume, c) providing a rear body assembly (100a) comprising a spring-driven drive ram assembly (310, 320) configured to drive the piston of a held cartridge (600, 600', 600"), d) providing a ram spacer member (400, 400', 400"), the ram spacer member defining a spacing geometry of length dimension (X1', X1", X1''', XS', XS", XS''', XR', XR", XR''') selected according to the fill volume of the cartridge (600, 600', 600"), and e) assembling a front body assembly (100b, 100c, 100c', 100c"), the cartridge (600, 600', 600"), the ram spacer member (400, 400', 400") and the rear body assembly (100a) so that the ram spacer member (400, 400', 400") is arranged axially between the drive ram assembly (310, 320) of the rear body assembly (100a) and the piston of a held cartridge (600, 600', 600").

27 Claims, 14 Drawing Sheets

Figure 1A:
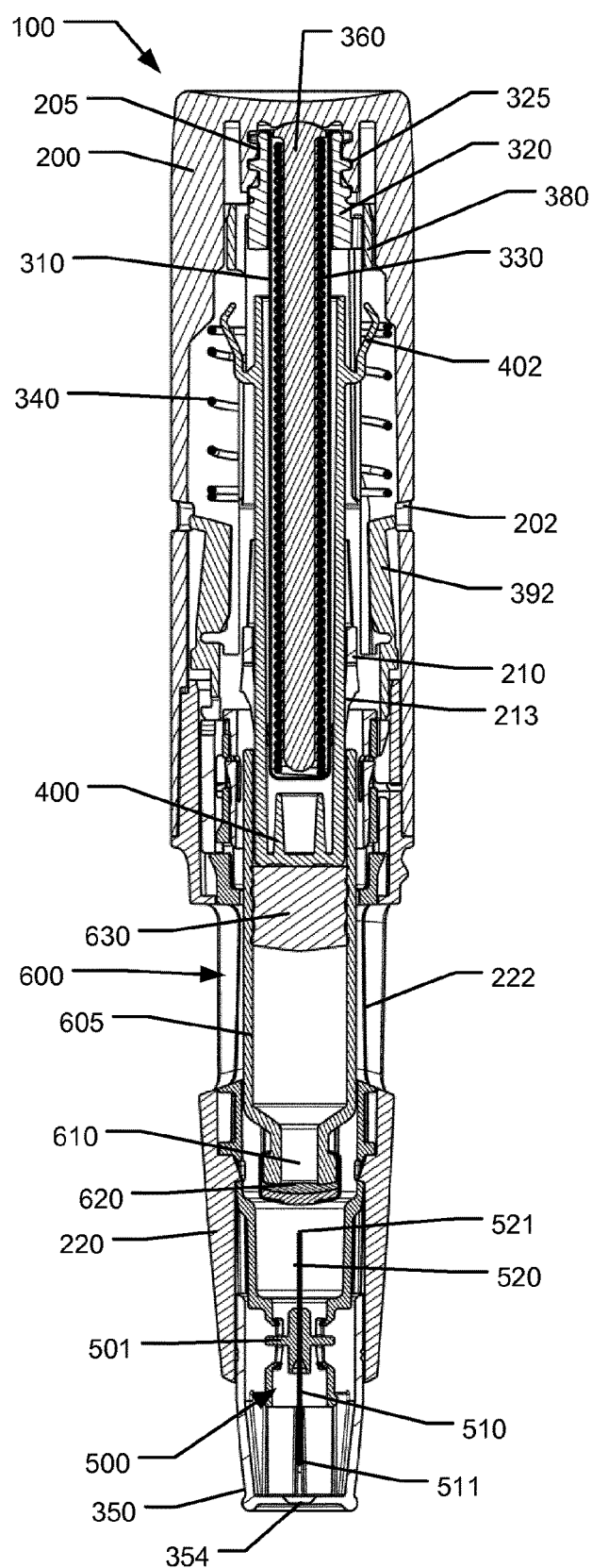

(51) Int. Cl.
*A61M 5/32* (2006.01)
*A61M 5/24* (2006.01)
*A61M 5/50* (2006.01)

(52) U.S. Cl.
CPC ...... *A61M 5/31585* (2013.01); *A61M 5/3234* (2013.01); *A61M 5/3245* (2013.01); *A61M 5/32* (2013.01); *A61M 5/3243* (2013.01); *A61M 5/50* (2013.01); *A61M 2005/2013* (2013.01); *A61M 2005/2073* (2013.01); *A61M 2005/247* (2013.01); *A61M 2005/2407* (2013.01); *A61M 2005/3247* (2013.01); *A61M 2005/3267* (2013.01); *A61M 2205/581* (2013.01); *A61M 2205/6081* (2013.01); *A61M 2207/00* (2013.01)

(58) Field of Classification Search
CPC .. A61M 5/3234; A61M 5/31585; A61M 5/50; A61M 5/3243; A61M 2005/206; A61M 2005/2013; A61M 2005/2026; A61M 2005/2073; A61M 2005/3126
See application file for complete search history.

(56) References Cited

U.S. PATENT DOCUMENTS

| | | | |
|---|---|---|---|
| 6,743,203 B1 | 6/2004 | Pickhard | |
| 7,449,012 B2* | 11/2008 | Young | A61M 5/2033 604/192 |
| 7,678,085 B2 | 3/2010 | Graf | |
| 7,717,877 B2 | 5/2010 | Lavi et al. | |
| 7,758,548 B2 | 7/2010 | Gillespie et al. | |
| 2004/0225262 A1 | 11/2004 | Fathallah et al. | |
| 2006/0264830 A1 | 11/2006 | Hommann | |
| 2007/0111175 A1* | 5/2007 | Raven | G09B 23/285 434/262 |
| 2010/0036320 A1 | 2/2010 | Cox et al. | |
| 2013/0310746 A1 | 11/2013 | Wozencroft | |
| 2014/0257197 A1 | 9/2014 | Madsen et al. | |

FOREIGN PATENT DOCUMENTS

| | | |
|---|---|---|
| CN | 102548599 A | 7/2012 |
| CN | 103442752 A | 12/2013 |
| EP | 1810616 A1 | 7/2007 |
| GB | 1528735 A | 10/1978 |
| WO | 2005044348 A1 | 5/2005 |
| WO | 2006062997 A1 | 6/2006 |
| WO | 2006063124 A2 | 6/2006 |
| WO | 2008116688 A1 | 10/2008 |
| WO | 2011003980 | 1/2011 |
| WO | 2011051365 A2 | 5/2011 |
| WO | 2012085588 A2 | 6/2012 |
| WO | 2012117255 | 9/2012 |
| WO | 2013152323 A1 | 10/2013 |

* cited by examiner

METHOD OF MANUFACTURING ONE OF A RANGE OF AUTOINJECTORS

CROSS-REFERENCE TO RELATED APPLICATIONS

This application is a 35 U.S.C. § 371 National Stage application of International Application PCT/EP2015/076466 (WO 2016/075254), filed Nov. 12, 2015, which claims priority to European Patent Application 14192895.2, filed Nov. 12, 2014; the contents of which are incorporated herein by reference.

FIELD OF THE INVENTION

The present invention relates to injection devices for injecting a medicament. In particular the present invention relates to autoinjector devices for injecting a medicament from a held cartridge and improvements relating to manufacturability of such injection devices.

BACKGROUND OF THE INVENTION

In relation to some diseases patients must inject a medicament on a regular basis such as once weekly, once daily or even a plurality of times each day. In order to help patients overcome fear of needles, fully automatic injection devices have been developed with the aim of making the use of the injection device as simple as possible. Such autoinjectors are typically designed such that a user shall position the injection device onto the injection site and activate the device.

Some autoinjectors further include a needle shield portion for shielding the needle before and/or after use. Disclosure of such devices is included in U.S. Pat. Nos. 7,449,012, 7,717,877 and WO2008/116688.

Different drugs may require different devices. It is difficult to develop one device that fits all drugs. Different parameters such as dose size, audible feedback (e.g. clicks), visual feedback (e.g. colour in drug window), a shield lock function, etc. depend of the particular application related to injection of a given drug. Therefore multiple devices are developed which is time consuming and costly.

As the particular design of an autoinjector may be targeted for a range of different applications relating to different medicaments and different therapy areas, a certain degree of variability may be aimed at. One particular reference US 2013/0310746 deals with modularizing parts of an autoinjector to provide a range of autoinjector of different fill volumes. However, the chosen design allows only little modularization.

Having regard to the above-identified prior art devices, it is an object of the present invention to enable manufacturing at a reduced cost.

BRIEF DESCRIPTION OF THE INVENTION

In a first aspect the present invention relates to a method of manufacturing one of a range of autoinjectors having cartridges with different preset fill volumes, the method comprising the steps of:
a) providing a front body assembly,
b) providing a cartridge of given fill volume, the cartridge being selected from a range of cartridges having different fill volumes, the cartridge comprising a cartridge body extending along an axis and a piston axially slideably arranged within the cartridge body, the cartridge body defining a distal outlet portion and a proximal open end,
c) providing a rear body assembly comprising a rear body housing, a drive ram assembly, and an actuator for providing a force arranged to act on the drive ram assembly to drive the piston of a held cartridge distally, whereby the drive ram assembly is releasably held relative to the rear body housing against the force of the actuator,
d) providing a ram spacer member, the ram spacer member defining a spacing geometry of length dimension (X1", X1", X1''', XS', XS", XS''', XR', XR", XR''') selected from a range of ram spacer members having spacing geometries of different length dimensions (X1", X1", X1''', XS', XS", XS''', XR', XR", XR''') according to the fill volume of the cartridge, and
e) assembling the front body assembly, the cartridge, the ram spacer member and the rear body assembly so that the ram spacer member is axially arranged between the drive ram assembly of the rear body assembly and the piston of a held cartridge.

In accordance with the first aspect, the ram spacer member is attached lately in the assembly line and defines much of the performance of the autoinjector. Hence, it is possible to develop and manufacture one device platform, containing mostly generic parts. Having a ram spacer member variant for each drug candidate enables a flexible and cost effective device development and device manufacturing line. At the same time, numerous features and parameters may be tailor-made by the modular design where the features and parameters are specifically adapted for the specific therapy application in question.

In accordance with the first aspect, the spacing geometry of the ram spacer member may be configured to separate the piston of a held cartridge from the distal end of the drive ram assembly by a predetermined distance (X1', X1", X1''') in accordance with the filing level or filling volume of the selected cartridge.

Alternatively, or in addition, the spacing geometry of the ram spacer member may comprise a dose stop surface arranged a distance (XR', XR", XR''') from a distal end surface of the ram spacer member in accordance with the filling level or filling volume of the selected cartridge. In accordance with the selected cartridge having a piston located at an initial position in the cartridge body said distance (XR', XR", XR''') may be selected in accordance with the axial distance between a proximal surface of the piston and a proximal end surface of the cartridge body. Thereby, after selecting a particular cartridge from the range of different cartridges, the effective stroke length (XS', XS", XS''') can be defined which is decisive volume of the dose that is expellable by the autoinjector.

In some embodiments, the rear body assembly may be of common design for each of the range of autoinjectors. In such embodiments, the rear body assembly provides a self-contained energized module which may be pre-assembled for long-term storage and later, upon final assembly, be coupled with one of a variety of different drug containers. Hence the rear body assembly may thus be utilized for a large variety of different autoinjectors each of which is applicable for a specific therapy application.

The assembled autoijector may be configured for operation so that upon release of the drive ram assembly from a held position relative to the rear body housing the force of the actuator drives the ram assembly causing the piston to be driven distally.

The method may further define that, in method step c) of providing the rear body assembly, the method comprises the steps of:

c1) providing the rear body housing, the drive ram assembly, the actuator and a trigger assembly,
c2) bringing the actuator into an energized state for establishing said force, and
c3) assembling the rear body housing, the drive ram assembly, the actuator and the trigger assembly while maintaining the actuator in the energized state, and arranging the trigger assembly in a locked state to releasably hold the drive ram assembly relative to the rear body housing against the force of the actuator.

In step c3), the method step of assembling the rear body housing, the drive ram assembly, the actuator and the trigger assembly while maintaining the actuator in the energized state may be performed by means of the trigger assembly.

In a further embodiment the trigger assembly comprises a first lock element and a trigger element spring, the first lock element being movably arranged relative to the rear body housing away from a locked position/locked state and into a triggering position, wherein the trigger element spring acts to bias the first lock element towards the locked position/locked state for maintaining the trigger assembly in the locked position/locked state.

The trigger element spring may be or may comprise a compression spring acting in compression mode to urge the first lock element towards the locked position/locked state. The trigger element spring may be arranged coaxially with the actuator. Where the actuator is provided as an actuating spring which takes the form of a helical spring, the trigger element spring may be arranged coaxially with and axially overlapping the actuating spring.

In further embodiments, the trigger assembly acts, prior to step e) of assembling the front body assembly with the rear body assembly, to maintain the trigger element spring in an initial compressed state. In still further embodiments, the trigger assembly acts to maintain the trigger element spring in an initial compressed state until triggering of the assembled autoinjector.

By arranging the trigger element spring in the rear body assembly, a particular large fraction of the total number components of the autoinjector may be included in the generic rear body assembly thereby reducing the number of assembly steps subsequent to the inclusion of the non-generic parts, e.g. the medicament cartridge, the ram spacer member etc.

In one embodiment the method step c2) of bringing the actuator into an energized state may be carried out prior to step c3). In other embodiments the step c2) may be performed during the assembly defined in step c3). In still other embodiments, the energizing of the actuator is partly carried out prior to step c3) and partly during the assembly defined in step c3).

The compression of the trigger element spring may be carried out while energizing of the actuator is performed. In still further embodiments, the energizing of the actuator and/or the compression of the trigger element spring is performed by means of relative movement of these components relative to the rear body housing during assembling operation with the rear body housing.

The method may further be defined so that the method step a) of providing the front body assembly comprises the steps of:
a1) providing a front body housing, a needle assembly and a needle shield for cooperation with the trigger assembly of the rear body assembly, and
a2) arranging the front body housing, the needle assembly and the needle shield relative to each other enabling the needle shield to move axially relative to the front body housing between an extended position and a collapsed position.

In some embodiments, the step a1) of providing a needle assembly is made by providing a cartridge having a needle assembly fixedly attached with the cartridge. Such cartridge and needle assembly may be provided as a pre-filled syringe. In other embodiments, the needle assembly may be provided as a needle assembly that is separately arranged relative to a pre-filled cartridge and wherein the needle assembly and the cartridge are configured for being subsequently coupled to allow fluid communication there between.

The method step a1) may include, prior to assembling the needle assembly and the needle shield relative to the front body housing, forming a needle assembly/needle shield sub-assembly, wherein a mechanism prevents relative axial movement between the needle assembly and the needle shield prior to assembling said needle assembly/needle shield sub-assembly with the front body housing. Said mechanism may be designed to cause said prevention of relative axial movement between the needle assembly and the needle shield to cease upon the needle assembly/needle shield sub-assembly being assembled with the front body housing, or alternatively upon the needle assembly/needle shield sub-assembly being assembled with the rear body assembly.

Typically, in known autoinjectors that incorporate triggering of the injection by moving a needle shield relative to a housing of the device, a separate spring element for biasing the needle shield towards an extended position is disposed in the distal part of the device.

However, in accordance with the first aspect, the trigger element spring may be included in the rear body assembly and the assembly operation as well as any tensioning of the trigger element spring may be carried out when assembling the generic rear body assembly.

In a further embodiment, subsequent or during step e), cooperation between the needle shield and the trigger assembly is enabled so that movement of the needle shield from the extended position into the collapsed position operates or causes to release the trigger assembly from the locked state enabling or causing the force of the actuator to operate the drive ram assembly.

In step e), a step of establishing a coupling between the needle shield and the first lock element may be provided so that relative axial movement between the needle shield and the first lock element is prevented. An exemplary embodiment of said coupling may be provided as an axial snap connection between the needle shield and the first lock element. However, other mounting means may alternatively be used.

The ram spacer member may in some embodiments define a single-part member. In alternative embodiments the ram spacer member may be formed as an assembly of multiple parts. In still further embodiments, the ram spacer member may be made adjustable so that different portions of the ram spacer member may be coupled relative to each other to allow adjustment of the spacing geometry of length dimension ($X1'$, $X1''$, $X1'''$, $XS'$, $XS''$, $XS'''$, $XR'$, $XR''$, $XR'''$). In accordance herewith differently adjusted ram spacer members may provide said range of ram spacer members.

The ram spacer member may be formed so that it defines an elongated plunging geometry. In further embodiments the drive ram assembly includes a longitudinal member which may be provided in the form of a drive ram. The elongated plunging geometry of the ram spacer member is dimensioned for being axially inserted into the proximal open end of the cartridge body. The ram spacer member defines a proximally facing axially extending opening dimensioned to receive the longitudinal member of the drive ram assembly.

In further embodiments, subsequent to step e), and where the drive ram assembly is held relative to the rear body housing against the force of the actuator, the longitudinal member of the drive ram assembly extends axially into the proximal open end of the cartridge body.

In further embodiments the longitudinal member of the drive ram assembly is partly or completely made from a metal alloy. In still further embodiments the actuator is provided as a helical compression spring arranged internally in a longitudinal bore of the longitudinal member of the drive ram assembly. By using a metal alloy for the longitudinal member this allows for reduced material dimensions of the longitudinal member which in turn allows for a larger springer to be used. At the same time non-problematic storage of the rear body assembly can be utilized wherein the actuator is held in the energized state during long-term storage.

In some embodiments the ram spacer member may define a click sound generating geometry configuration which associates with a cooperating click sound geometry configuration of another component of the autoinjector which, subsequent to release of the drive ram assembly, generates a predetermined sequence of clicks.

In step d) of providing the ram spacer member, the method step may include the selection of a ram spacer member from the range of ram spacer members having differing click sound generation geometries. A first click sound geometry configuration of the selected ram spacer member is configured for cooperating with a second click sound geometry configuration associated with the housing of the autoinjector to generate at least one click sound at the start, during or at the end of the dose expelling operation. In some variants, a single or a multitude of click sounds are generated during the expelling movement, e.g. as the spacer member is displaced relative to the cartridge. Alternatively, or in addition, a single or a multitude of click sounds may be generated as a cartridge of the autoinjector is moved relatively to the housing of the autoinjector.

In a further embodiment the ram spacer member defines a distal facing surface configured to cooperate with the piston of a held cartridge and defines a proximally facing abutment surface arranged in the proximal opening to cooperate with the longitudinal member of the drive ram assembly, and wherein said length dimension (X1', X1", X1''') defines the axial extension between the distal facing surface and the abutment surface. By selecting a proper length dimension (X1', X1", X1''') unintentional axial slack between components may be avoided. This reduces the risk of potential damage to the cartridge and serves to reduce unwanted noises which may occur during triggering of the autoinjector.

In a further embodiment the ram spacer member comprises an end of dose stop surface adapted to cooperate with an end of stroke stop geometry associated with the cartridge to limit distal movement of the ram spacer member relative to the cartridge body of a held cartridge.

In a further embodiment the end of dose stop surface of the ram spacer member is a distally facing surface disposed at a location having a predetermined distance from the distal facing surface of ram spacer member, wherein the end of dose stop surface is configured for cooperating with a proximal end of the cartridge body to limit the stroke of movement of the ram spacer member relative to the cartridge body.

In a further embodiment the rear body housing of the rear body assembly defines a distally arranged opening leading into a cavity, and wherein the cavity fully accommodates the trigger assembly. Since the rear body assembly may be provided as an assembly where the trigger assembly does not protrude outside the cavity of the rear body housing, the risk of unintentional triggering during subsequent handling steps can be markedly reduced.

In further embodiments, the remaining parts of the rear body assembly, e.g. the drive ram assembly and the actuator, are kept fully within the bordering walls of the rear body housing to provide a sub-assembly which may be stored and safely handled during subsequent assembly operations.

In further embodiments, the step d) of providing a ram spacer member may include the step of selecting the colour of a coloured ram spacer member from a range of differently coloured ram spacer members. The colour of the ram spacer member, such as the colour of a coloured portion of the ram spacer member may be used to signify the contents of the cartridge.

For the assembled autoinjector that includes such coloured ram spacer member an exterior view may be provided to at least a portion of the coloured ram spacer member, such as through a window or through one or more transparent sections. The exterior view of the coloured ram spacer member may be provided either before and/or after triggering. As such an increasing portion of the coloured ram spacer member may become visible as the expelling operation progresses.

In a second aspect the present invention relates to an autoinjector that is provided by any of the methods according to the first aspect of the present invention.

In further aspects such autoinjector may include any of the following features.

In some embodiments the autoinjector may comprise:
a base,
a drug cartridge arranged relative to the base, the cartridge comprising:
a) an elongated body having a distal end and a proximal end and defining a central longitudinal axis, the body having a distally arranged outlet adapted for connection to a needle, and
b) a piston accommodated in the body, the piston configured for being driven axially in the distal direction to expel a dose of a drug through the outlet,
a plunger adapted for cooperation with the piston,
an actuator for providing a force and arranged to act on the plunger to drive the piston distally,
a needle shield axially movable relative to the base between an extended position and a collapsed position,
wherein the autoinjector defines a lock configured for releasably maintaining the plunger in an initial axial position against the force of the actuator, the lock being operated by the needle shield,
wherein the plunger is associated with a plunger thread component and wherein the base defines a base thread component adapted for operatively coupling with the plunger thread component,
wherein prior to activation, a) the plunger thread component is operatively coupled with the base thread component and b) the lock acts to prevent relative rotation between the plunger thread component and the base thread component, thereby maintaining the plunger in the initial axial position, and
wherein the lock is so configured that, upon the needle shield being moved towards the collapsed position, the lock is released enabling relative rotation between the plunger thread component and the base thread component causing release of the plunger from the initial axial position and expelling the dose of the drug.

In such autoinjector, the device may include a needle shield triggered expelling assembly where the actuator, such as a pre-stressed actuating spring, is actuated for releasing axial movement of the plunger by a movement of the needle shield relative to the base. According to some embodiments, as the energy accumulated in the actuator is not changed when the needle shield is moved axially from the extended position to the collapsed position, the force exerted on the needle shield for performing this movement does not induce a movement of the plunger against the force provided by the actuator. Hence, in particular for autoinjectors having an actuator configured for exerting a large force on the plunger, such as autoinjectors for expelling high-viscosity liquids or autoinjectors configured for use with thin injection needles, the movement of the needle shield is largely unhindered by the force provided by the actuator.

The autoinjector may be so configured that, prior to release of the lock while operatively coupling between the base thread component and the plunger thread component is maintained, the force applied by the actuator transfers into a force having a force component that acts to rotate the base thread component and the plunger thread component relative to each other. Apart from forces exerted by a possible needle shield spring, only frictional forces attributable to moving needle shield components needs to be overcome when moving the needle shield for triggering the expelling assembly.

The lock may be configured to include engaging first and second components having cooperating geometries that prior to activation engage to maintain the lock and which upon activation disengage and where the disengagement does not incorporate deformation of the cooperating geometries.

The cartridge body may define a proximally facing rear surface. The distally arranged outlet of the cartridge may comprise a pierceable septum adapted to be pierced by the rear needle of a needle unit having both a front needle extending in the distal direction and a rear needle extending in the proximal direction. In alternative configurations, the cartridge body outlet portion includes an injection needle fixedly attached relative to the cartridge body.

In some embodiments, the base forms a housing of the device. The autoinjector may accommodate a needle that is fixedly mounted relative to the base.

In some embodiments, the front needle is configured to be manually operable relative to the needle shield such that when the needle shield is held against an injection site, manual operation of the front needle relative to the needle shield or vice versa causes manual penetration of the front needle into the injection site and causes subsequent release of the lock.

By configuring the device so that a pushing force exerted manually on a part of the device is transferred to a manual force acting on the needle for manual penetration of the front needle into the injection site, the user gains improved control of the insertion of the injection needle. At the same time, by using this configuration the needle is hidden from the user during an administration. By providing an improved control of the needle insertion procedure a potential uneasiness for the user can be alleviated. The first part of the activation movement moves the needle forward relative to the needle shield to insert the needle in the user's skin. The second part of the movement activates the expelling assembly. In particular embodiments, this allows the user to manually insert the front tip of the needle before activating the device and an administration may be stopped in time should the user wish to abort the operation.

Relative rotational movement between the plunger thread component and the base thread component may be performed around a first rotational axis. In some embodiments the first rotational axis is arranged coaxially with respect to the central longitudinal axis of the body of the cartridge. In other embodiments, the first rotational axis and the central longitudinal axis are arranged non-coaxially with respect to each other.

In the context of the present disclosure, when referring to "a base thread component", "a plunger thread component", and "a base thread component being adapted for operatively coupling with the plunger thread component" this shall be so construed that when the plunger thread component is operatively coupled with the base thread component the relative movement between the plunger thread component and the base thread component is provided by means of a helical guiding movement. Non-limiting examples of a helical guiding movement includes a threaded coupling and a track and track follower coupling. A threaded coupling may be provided by means of co-operating screw threads having a constant lead along the first rotational axis or a variable lead along the first rotational axis. A threaded component may be provided by means of a continuous threaded section or by means of a plurality of thread segments. A track and track follower coupling may define a track having a constant pitch relative to said first rotational axis or a track having a varying pitch along the first rotational axis.

When the helical guiding movement is provided by a threaded coupling, the threaded coupling may be formed as a non-self-locking threaded coupling.

The plunger thread component may be provided as an outer thread extending radially outwards from the plunger thread component and configured to engage an inner thread provided by the base thread component. Alternatively, the plunger thread component may define an inner thread component extending radially inwards from a side surface portion of an axial bore of the plunger thread component configured to engage an outer thread provided by the base thread component. In some embodiments the thread component is formed by the plunger, such as being fixedly attached to the plunger or integrally formed with the plunger.

The needle may incorporate a sterility barrier for the front needle. In applications where a rear needle is present, a sterility barrier for the rear needle or for both the front needle and rear needle may be incorporated. In some embodiments, the sterility barrier may be formed as a flexible cover or sheath configured as a closed cavity for accommodating at least a part of the needle, i.e. the front needle or the rear needle.

The injection device may comprise an actuator in the form of a stored energy source coupled to the plunger and configured for driving the plunger upon release of the lock. Non-limiting examples of a stored energy source include a spring element, such as a pre-strained spring, a compressed gas etc., wherein the stored energy may be accumulated during manufacture of the autoinjector. In other forms, the energy source is configured to become charged during an initial operation of the device prior to activation of the injection mechanism. The stored energy source stores sufficient energy to operate the autoinjector for expelling the total amount of drug that is intended to be expelled from a held cartridge, and, optionally, surplus energy for driving the cartridge forward for coupling to a rear needle and/or for driving the needle shield for a needle shielding operation.

In particular forms, the actuator is provided as a helical compression spring that exerts an axial force on the plunger. In alternative forms, the helical compression spring is configured to additionally exert a torque acting to rotate the plunger thread component and the base thread component relative to each other.

The plunger may include a drive ram. Further, the plunger may include a ram spacer member for the drive ram positioned between the drive ram and the piston of the held cartridge. In some embodiments of the autoinjector the actuating spring is a helical compression spring arranged internally in a longitudinal bore of the drive ram. The drive ram may be made from a metal alloy, such as stainless steel. Alternatively, the drive ram may be made from a plastic material.

In some embodiments the autoinjector may include a needle shield spring which is associated with the needle shield and the needle to urge the front needle into its shielded state or to urge the needle shield into the state where the front needle is shielded. In particular embodiments the needle shield spring is an element separate from the actuator or the actuating spring. Exemplary non-limiting embodiments of a needle shield spring include springs such as a helical spring acting in compression mode and/or torsion mode, a leaf spring, a plastic spring or a plastic material spring element formed separately or integrally with other components of the autoinjector.

In some embodiments of the autoinjector, the lock includes a first lock element that is axially movable as the needle shield moves from the extended position towards the collapsed position, wherein the first lock element and the plunger thread component define respective cooperating lock geometries configured to, prior to activation, maintain a rotational lock between the plunger thread component and the base, the cooperating lock geometries being adapted to unlock to enable rotation between the plunger thread component and the base thread component upon the needle shield being moved towards the collapsed position.

The first lock element may be formed integrally with the needle shield, as part of a needle shield sub-assembly or alternatively as a component separate from the needle shield but being operated by movement of the needle shield.

In particular embodiments of the autoinjector the first lock element is prevented from rotating relative to the base. The first lock element and the plunger thread component may define respective cooperating lock geometries configured to, prior to activation, maintain a rotational lock between the plunger thread component and the first lock element, the cooperating lock geometries being adapted to unlock to enable rotation between the plunger thread component and the first lock element upon the needle shield being moved towards the collapsed position.

In alternative embodiments the first lock element is allowed to rotate relative to the base when the needle shield has been pressed into its collapsed position but is prevented from rotating relative to the base when the needle shield is in the extended position. The first lock element and the plunger thread component define respective cooperating geometries configured to prevent relative rotation but allowing axial displacement.

It is to be noted that, in accordance with one aspect of the invention, the lock needs only to remain enabled, that is to remain in locking mode, in the initial storage state, i.e. prior to activation of the expelling assembly. After activation of the expelling assembly the lock is not required to enter into locking mode again, i.e. the lock elements need not prevent relative rotation between the plunger thread component and the base thread component as the needle shield is returned to its extended position.

In some embodiments of the autoinjector the base thread component is fixedly disposed relative to the base, such as by being formed integrally with the base. When the base defines the housing or a section of the housing, the base thread component is thus axially and rotationally fixed relative to the housing.

In some embodiments the first lock element defines a first lock feature and the plunger thread component defines a cooperating lock feature, wherein one of the first lock feature and the cooperating lock feature defines an axial track and wherein the other of the first lock feature and the cooperating lock feature defines a track follower. In such embodiment the axial track may be formed as a track that extends in a direction parallel with the first rotational axis. Hence, when the needle shield is moved from the extended position towards the collapsed position, the lock is released without inducing a relative rotation between the first lock element and the plunger thread component. Only subsequent to release of the lock, i.e. when the track follower disengages the track, is rotation between the first lock element and the plunger thread component is enabled. Thereafter rotational movement between the plunger thread component and the base thread component is induced by the force exerted by the actuator due to the operative coupling of the threaded connection.

In other embodiments, instead of said axial track extending in a direction parallel with the first rotational axis, the axial track may be formed to extend at an angle with respect to the first rotational axis, such as less than 20 degrees, alternatively less than 15 degrees, alternatively less than 15 degrees, and still alternatively less than 5 degrees. Such slightly angled axial track would in particular applications be acceptable as only a limited rotation between the plunger thread component and the base thread component would be induced during axial displacement of the needle shield.

In other alternative embodiments of the autoinjector, wherein the base forms part of or defines a housing of the autoinjector, the base thread component is defined by a rotatable component that is axially fixed but rotatably mounted relative to the base. The lock includes a first lock element that is axially movable as the needle shield moves from the extended position towards the collapsed position. The first lock element and the rotatable component define respective cooperating lock geometries configured to, prior to activation, maintain a rotational lock between the rotatable component and the plunger thread component, the cooperating lock geometries being adapted to unlock to enable rotation between the rotatable component and the plunger thread component upon the needle shield being moved towards the collapsed position.

The first lock element may be prevented from rotating relative to the base. The first lock element and the rotatable component define respective cooperating lock geometries configured to, prior to activation, maintain a rotational lock between the rotatable component and the first lock element, the cooperating lock geometries being adapted to unlock to enable rotation between the rotatable component and the first lock element upon the needle shield being moved towards the collapsed position. In such embodiments the plunger thread component may be prevented from rotating relative to the base. In such embodiments the plunger may be mounted non-rotationally relative to the base and the plunger thread component may be fixedly disposed on the plunger.

In some embodiments the first lock element defines a first lock feature and the rotatable component defines a cooperating lock feature, wherein one of the first lock feature and the cooperating lock feature defines an axial track and wherein the other of the first lock feature and the cooperating lock feature defines a track follower. In such embodiment the axial track may be formed as a track that extends in a direction parallel with the first rotational axis. Hence, when the needle shield is moved from the extended position towards the collapsed position, the lock is released without inducing a relative rotation between the first lock element and the rotatable component. Only subsequent to release of the lock, i.e. when the track follower disengages the track, rotation between the first lock element and the rotatable component is enabled. Thereafter rotational movement between the rotatable component and the plunger is induced by the force exerted by the actuator due to the operative coupling of the thread components of the rotatable component and the plunger.

In other embodiments, instead of said axial track extending in a direction parallel with the first rotational axis, the axial track may be formed to extend at an angle with respect to the first rotational axis, such as less than 20 degrees, alternatively less than 15 degrees, alternatively less than 15 degrees, and still alternatively less than 5 degrees. In particular applications, such slightly angled axial track would be considered acceptable as only a limited rotation between the plunger thread component and the base thread component disposed on the rotatable component would be induced during axial displacement of the needle shield.

In some embodiments of the autoinjector the plunger thread component is only operatively coupled with the base thread component during an initial first axial displacement of the plunger whereas, in a second axial displacement, the plunger thread component is released from being operatively coupled with the base thread component allowing the plunger to subsequently continue axial displacement.

Subsequent to axial release of the plunger, the end of stroke position of the plunger may be provided by a pre-determined axial stop position of the plunger relative to the proximally facing rear surface of the cartridge. The autoinjector may be so configured that a stop geometry of the plunger directly engages the proximally facing rear surface of the cartridge. Alternatively, one or more intermediary components may be positioned between the plunger and the proximally facing rear surface of the cartridge to provide said pre-determined predetermined axial stop position of the plunger relative to the proximally facing rear surface of the cartridge.

In some embodiments of the autoinjector the plunger thread component comprises a geometry having a radial dimension, such as a diameter, that is larger than the internal diameter of a cylindrical section of the cartridge. In particular for autoinjectors having an actuator that stores a large amount of energy, the large dimensions of the plunger thread component enable a robust design that offers non-problematic long-term storage, even in situations where one or both of the thread components are made from a non-metallic material and where the actuator during long-term storage is kept in a pre-tensed state.

In particular embodiments, where the housing of the autoinjector has a total length of dimension L, the base thread component may be arranged to extend from the proximal end of the housing. The base thread component may be arranged to extend from the proximal end of the housing by less than 30% of L, alternatively less than 20% of L, alternatively less than 10% of L, and still alternatively less than 5% of L.

In particular embodiments, the plunger thread component may dimensioned to extend from the proximal end of the plunger in the distal direction along the plunger by a length corresponding to less than 75% of the entire plunger length, alternatively by a length corresponding to less than 50% of the entire plunger length, alternatively by a length corresponding to less than 25% of the entire plunger length, and still alternatively by a length corresponding to less than 15% of the entire plunger length.

In some embodiments of the autoinjector the plunger thread component is located at the proximal end of the plunger. In some embodiments the plunger and the plunger thread may be formed as a unitary component. In other embodiments the plunger thread component may be formed as a release nut arranged at a fixed axial location on the plunger. The release nut may be freely rotatable relative to the plunger. In such embodiments, the plunger may be so configured that it does not rotate relative to the base, e.g. by being rotationally locked relative to the base either by means of cooperating locking geometries or by means of friction.

In some embodiments of the autoinjector the device irreplaceably accommodates a cartridge within the base and wherein the cartridge cannot be removed from the device without the use of tools.

In some embodiments of the autoinjector the force acting for causing rotation between the plunger thread component and the base thread component for releasing the plunger from the initial axial position is at least partly exerted by the actuator. In particular embodiments, the force acting for causing rotation between the plunger thread component and the base thread component for releasing the plunger from the initial axial position is exclusively exerted by the actuator.

In some embodiments, an externally applied force on the needle shield for causing the needle shield to be moved into the collapsed position is not transmitted into a force component acting to cause rotation between the plunger thread component and the base thread component for releasing the plunger from the initial axial position.

In embodiments incorporating a cartridge and a separate needle unit, the cartridge and the needle unit may be initially held in a configuration where the cartridge and the needle unit is separated by a distance. The actuator may be capable, upon release of the lock, to cause the cartridge and the rear needle to enter into the state where the cartridge septum is pierced by the rear needle and subsequently to cause the plunger to move to dispense the medicament through the needle.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figure 1B:
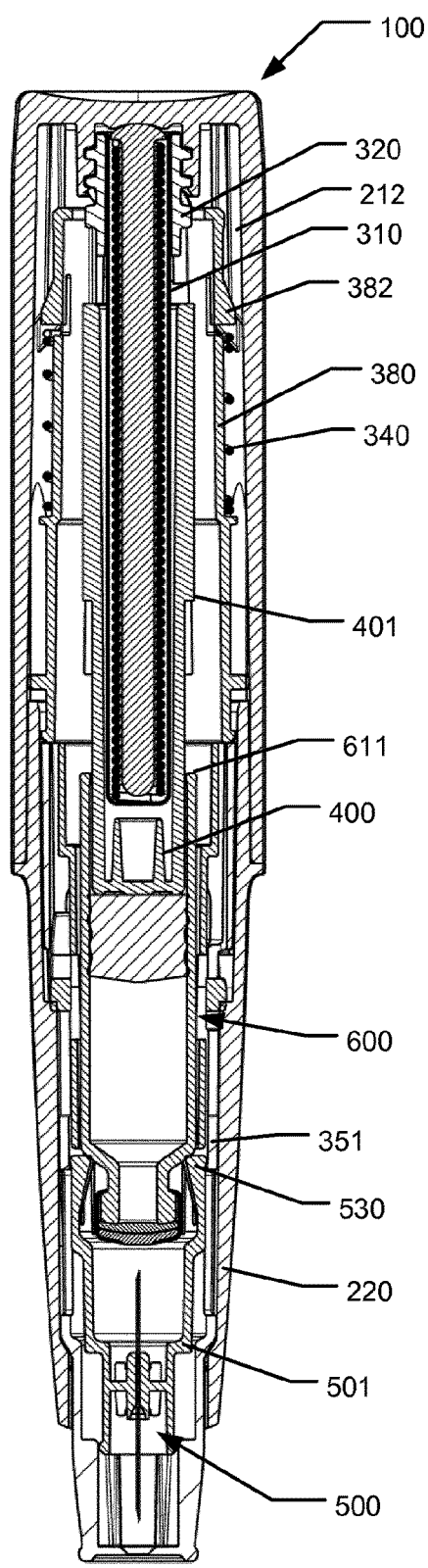
Figure 1C:
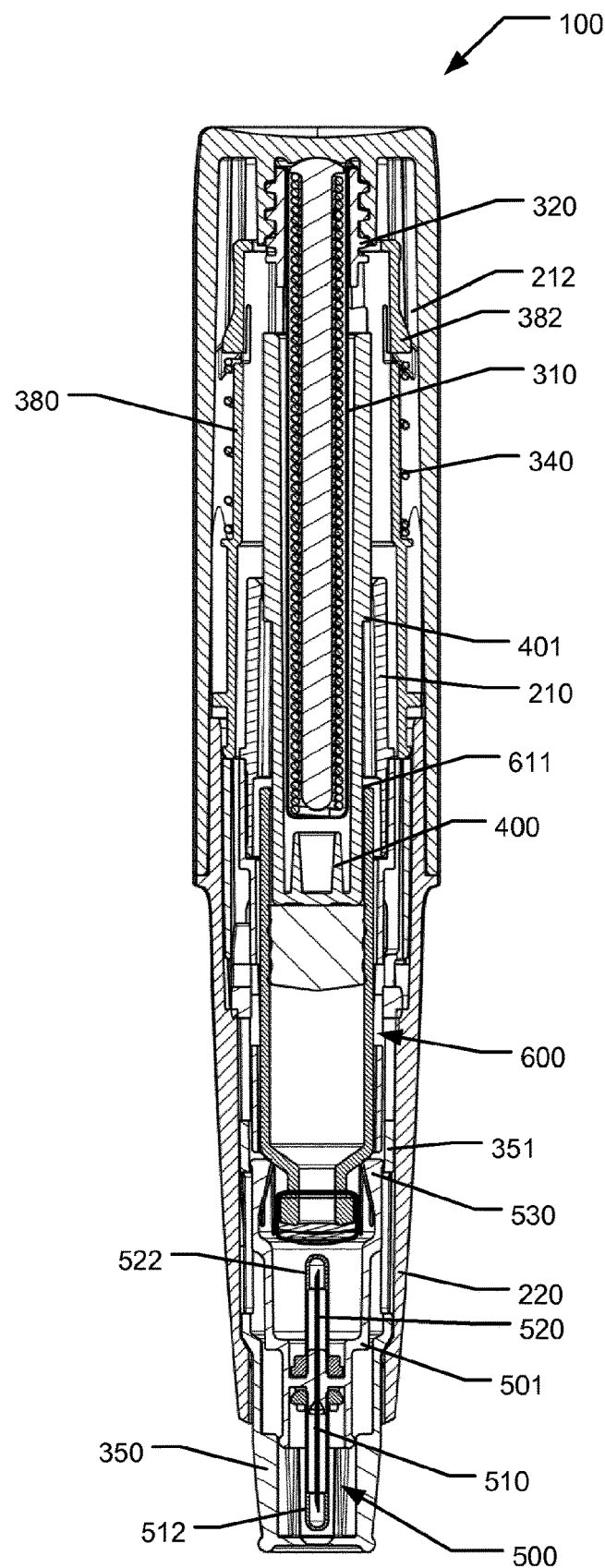
Figure 2A:
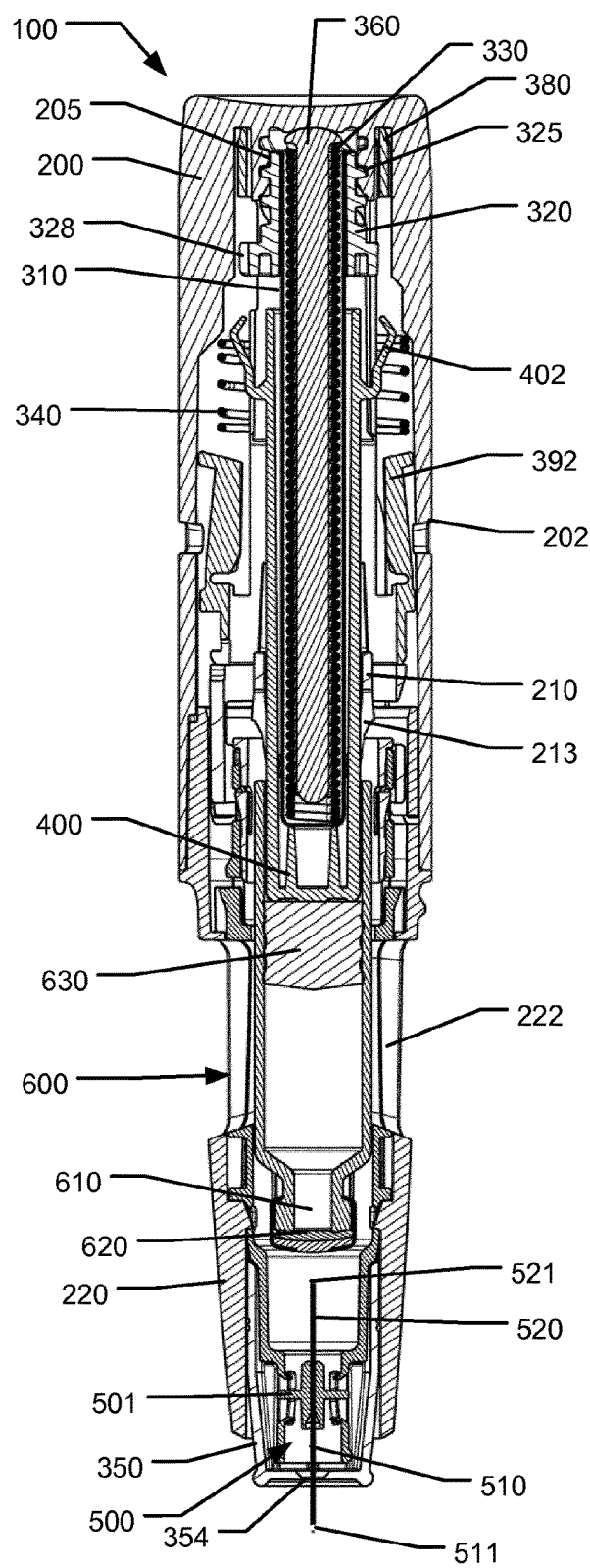
Figure 2B:
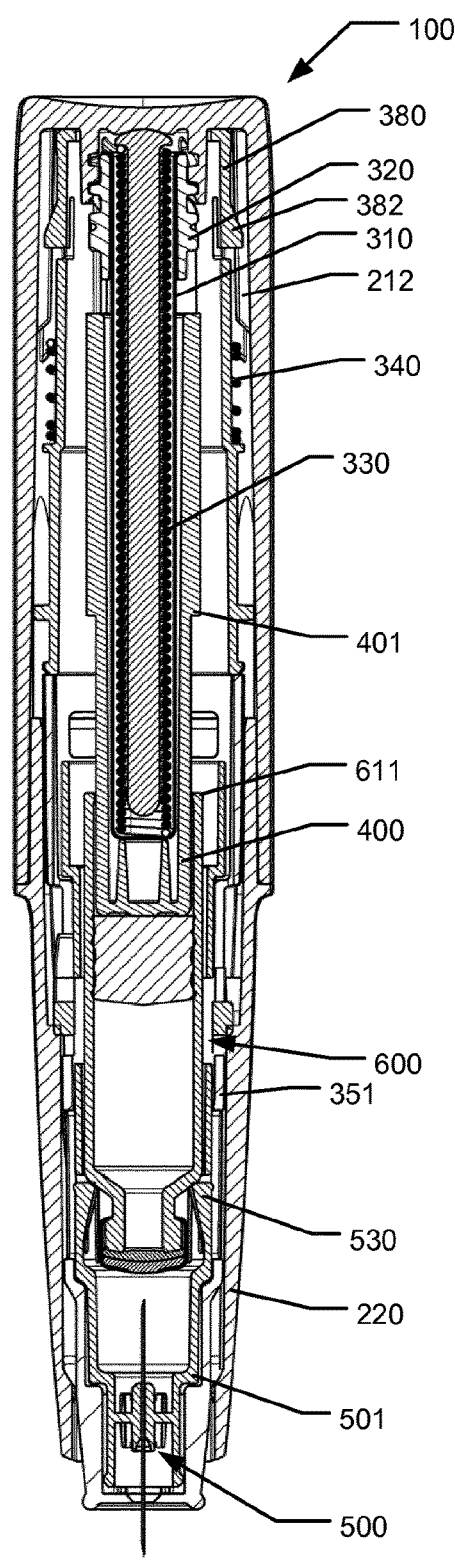
Figure 2C:
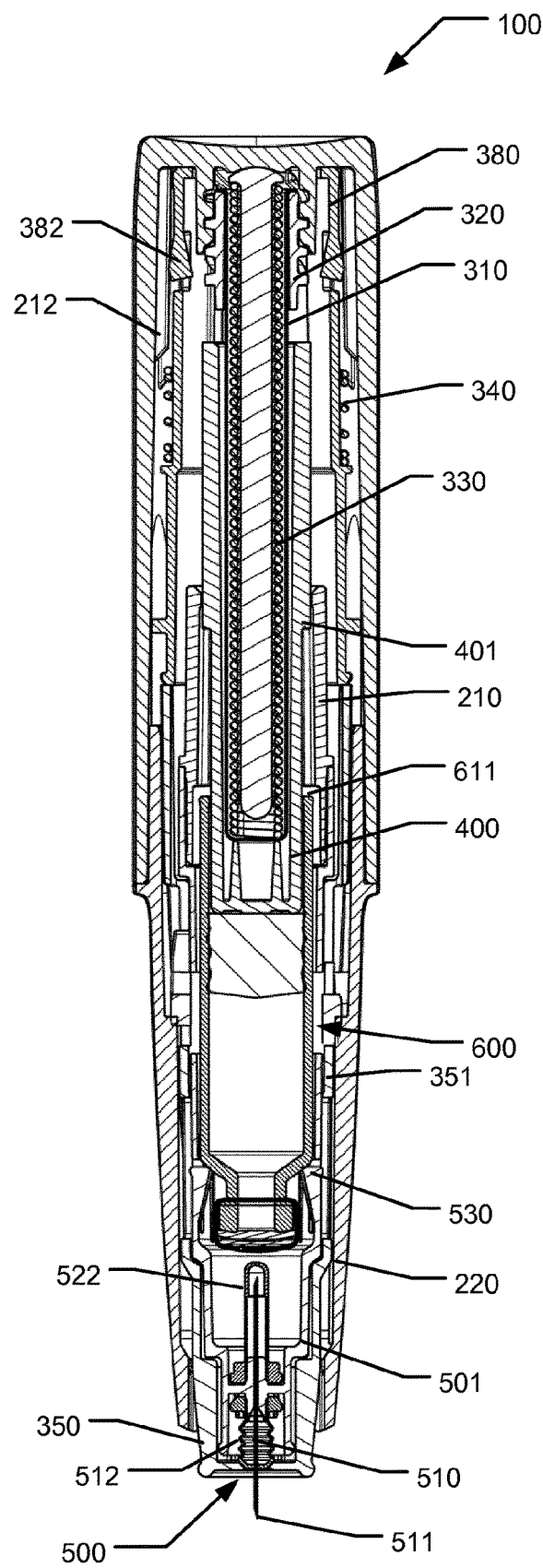
Figure 3A:
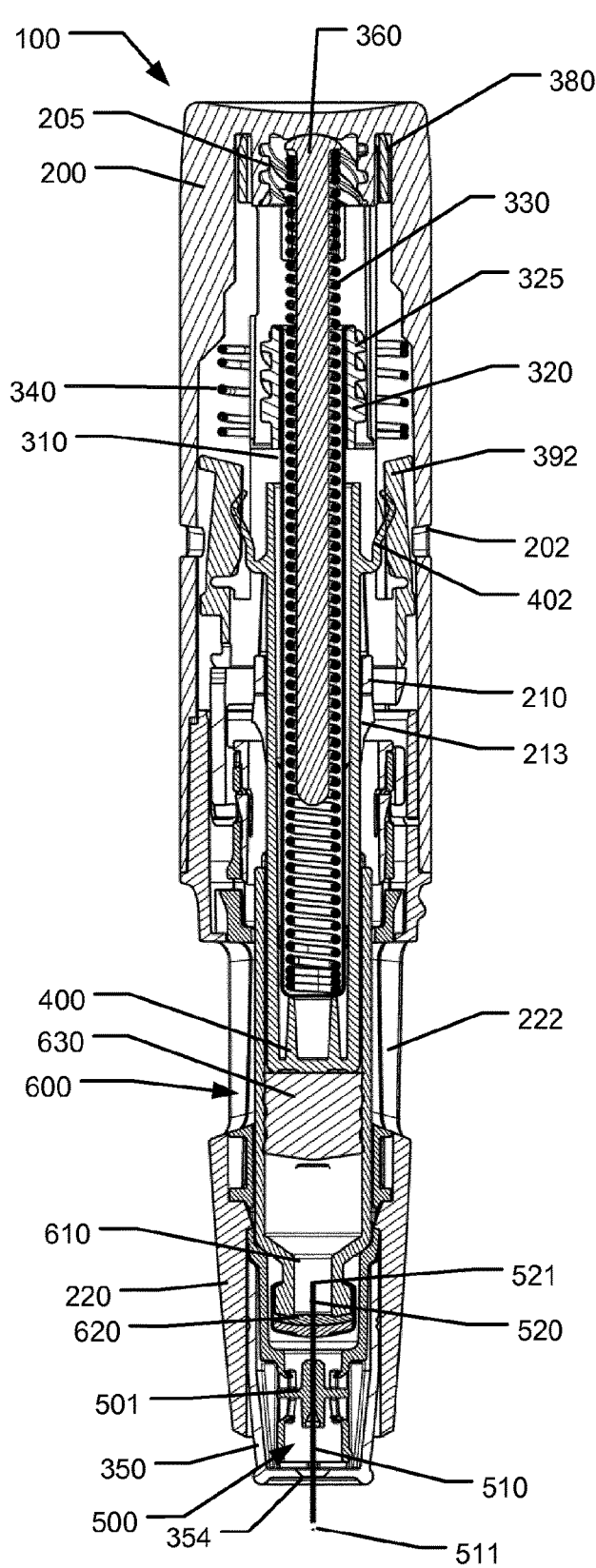
Figure 3B:
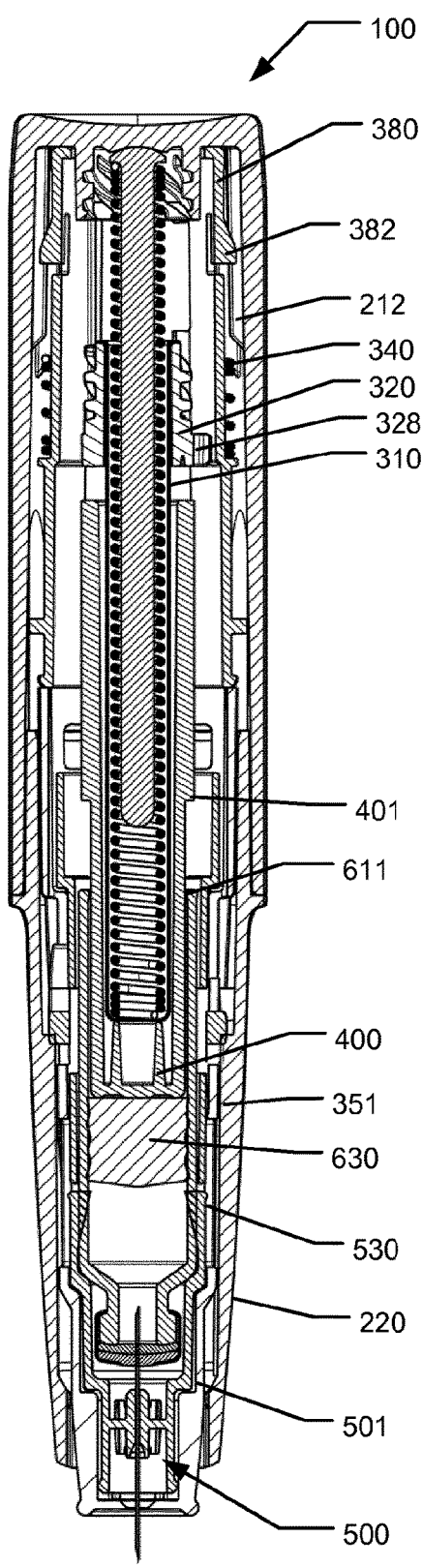
Figure 3C:
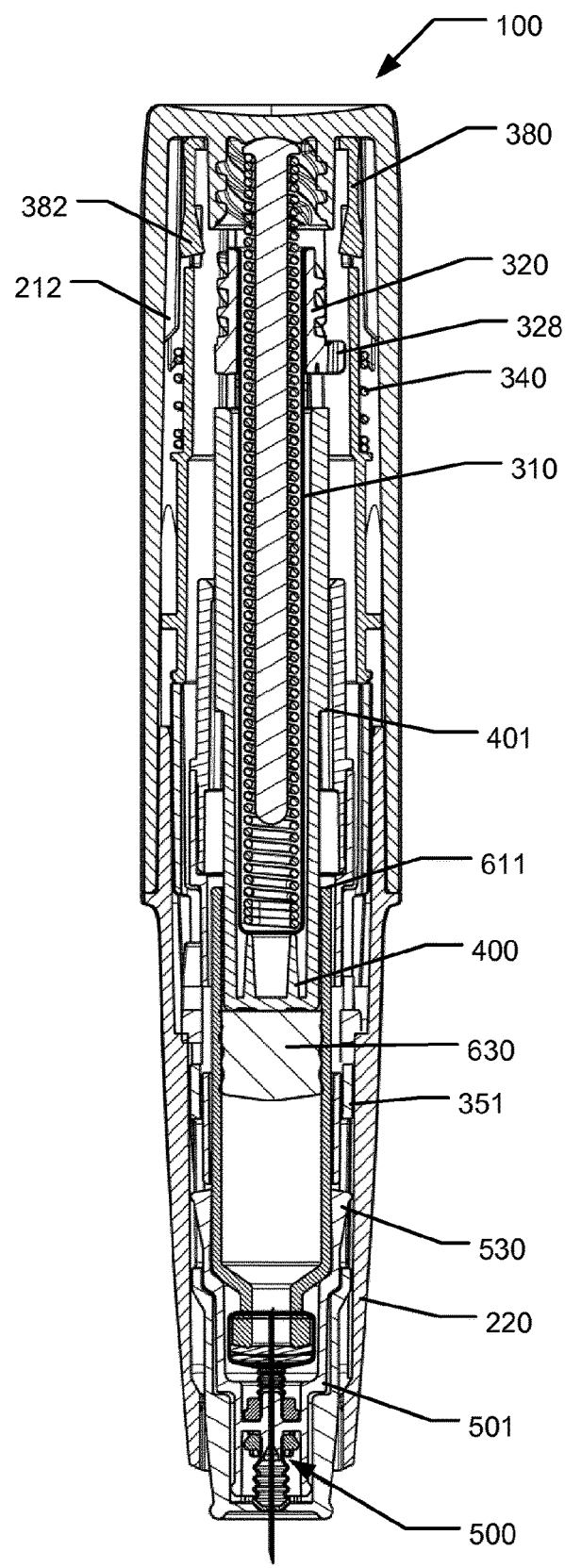
Figure 4A:
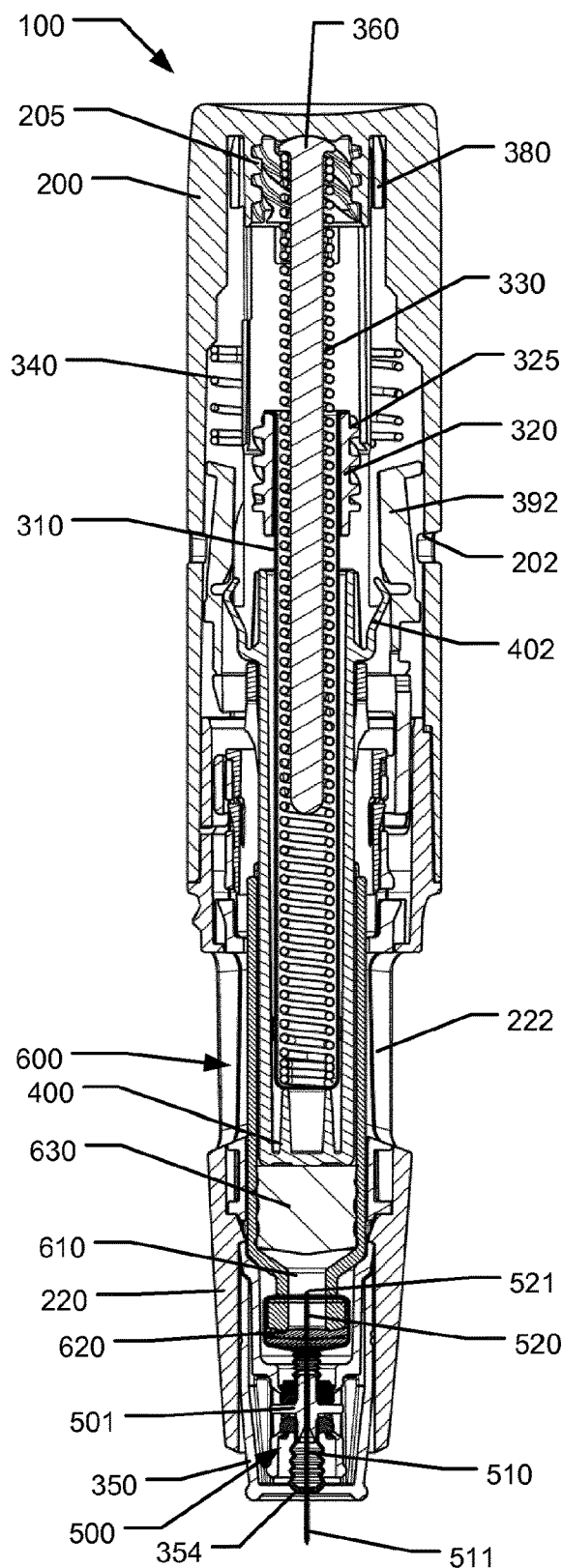
Figure 4B:
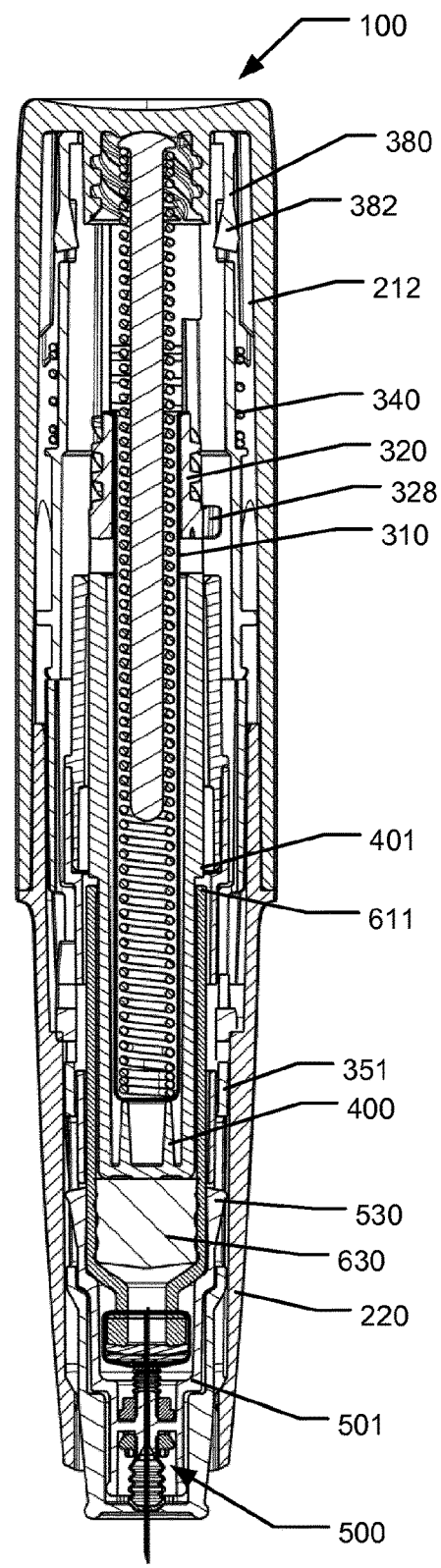
Figure 5A:
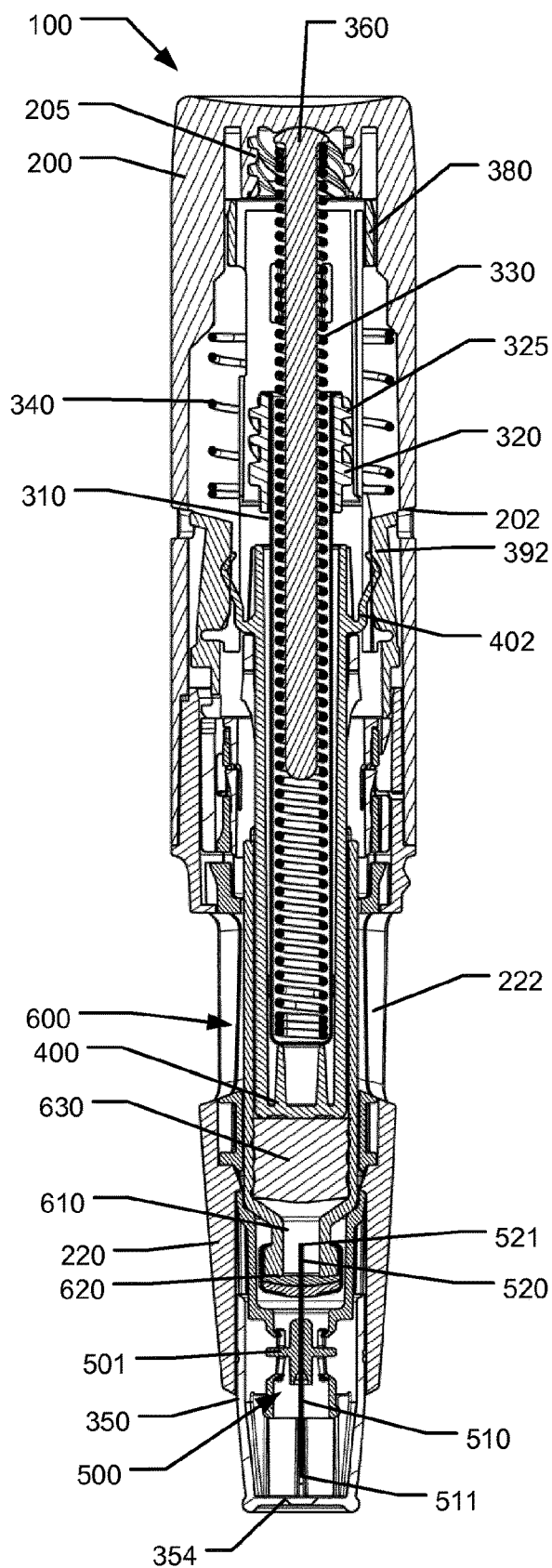
Figure 5B:
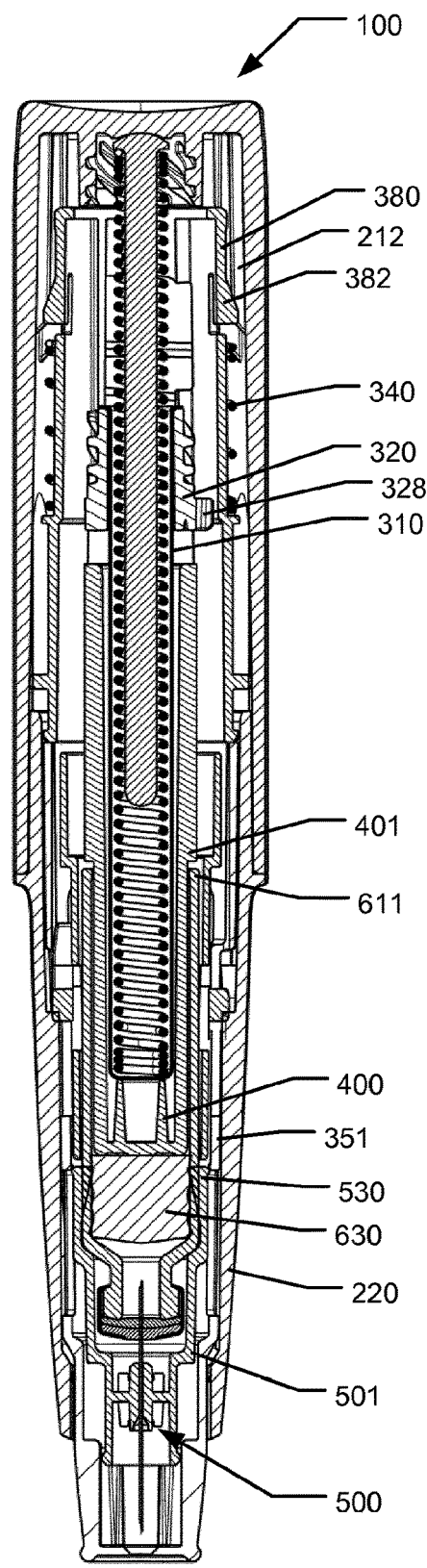
Figure 5C:
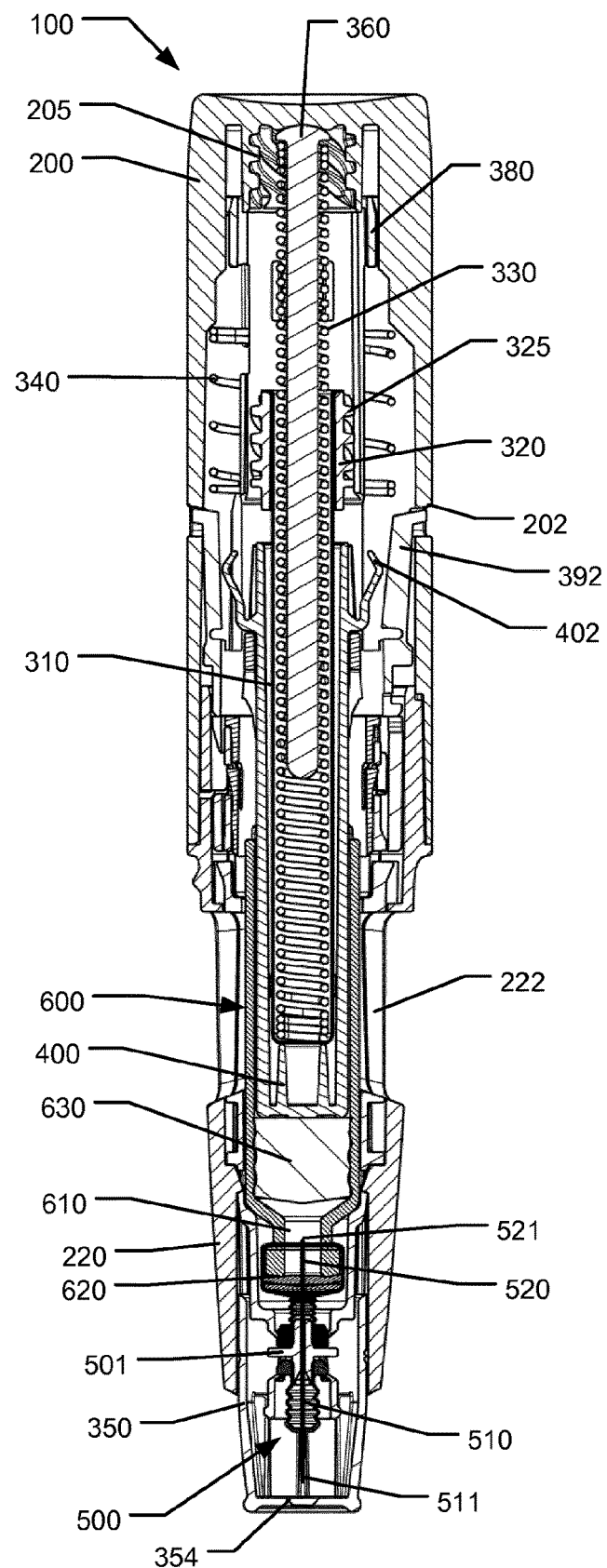
Figure 6:
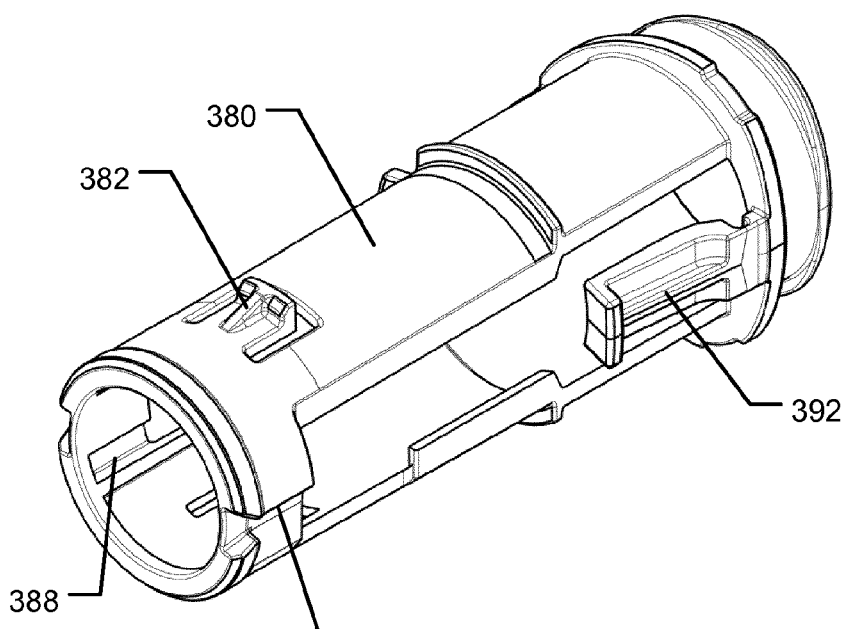
Figure 7:
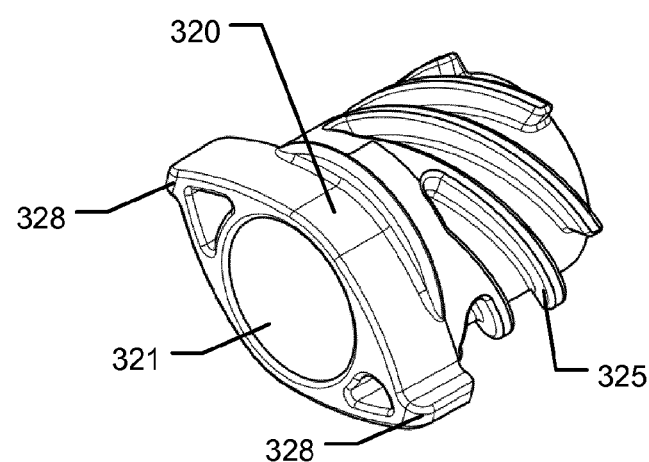
Figure 8:
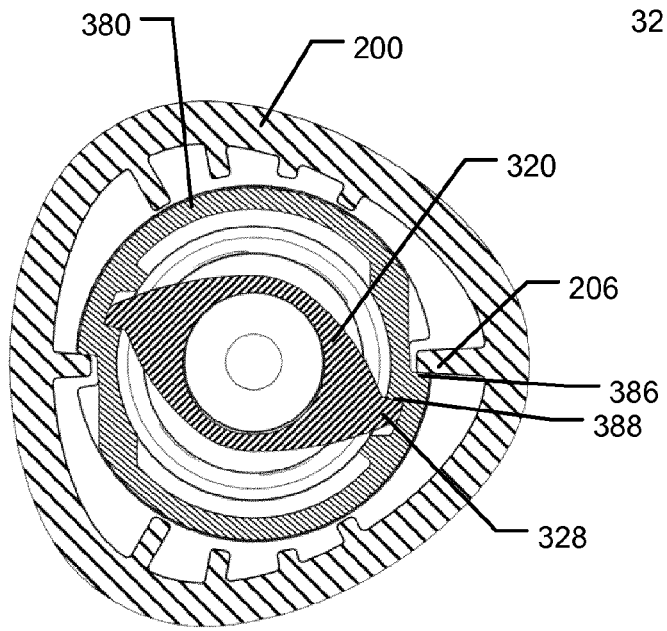
Figure 9A:
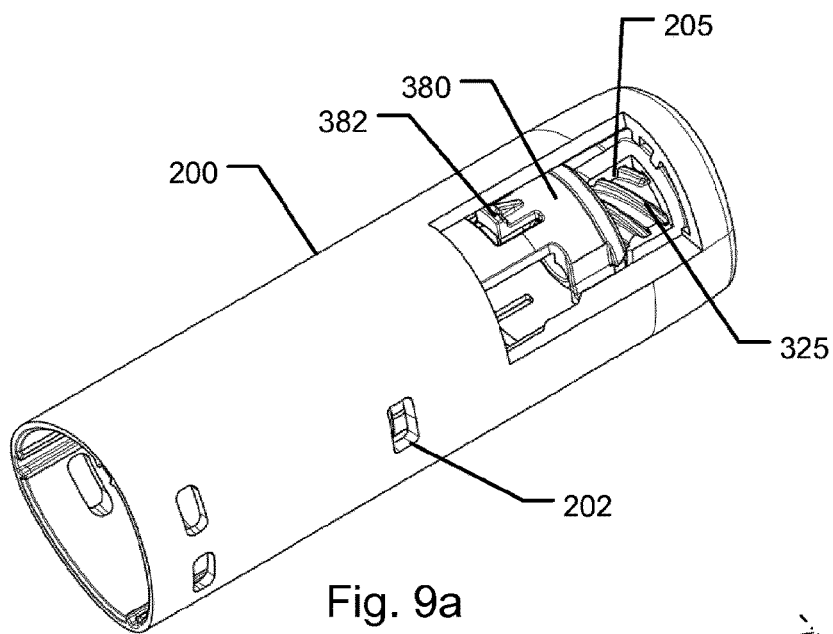
Figure 9B:
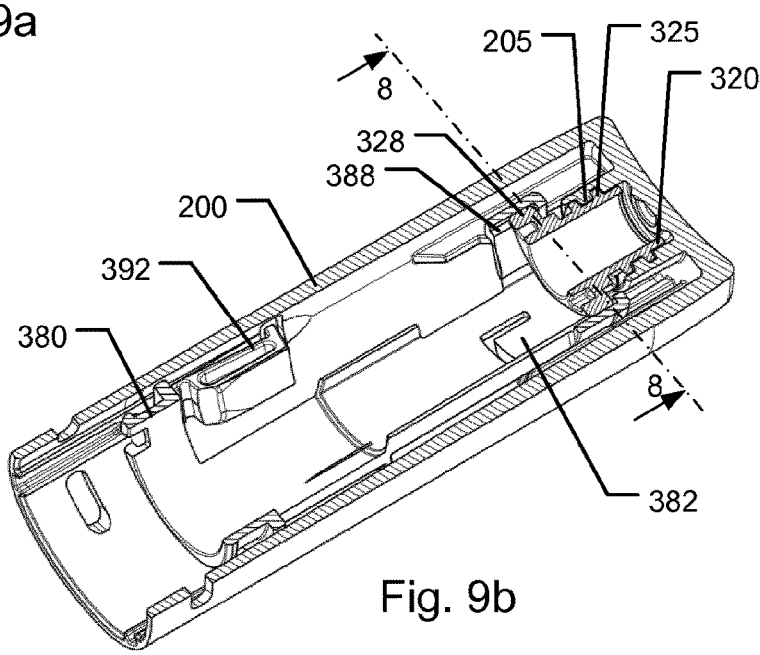
Figure 9C:
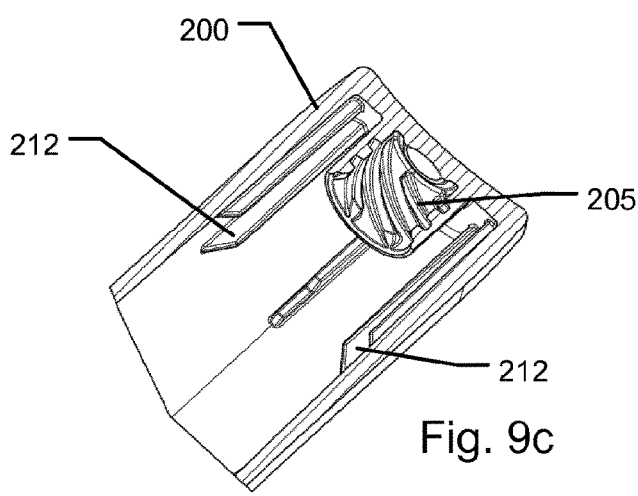
Figure 10:
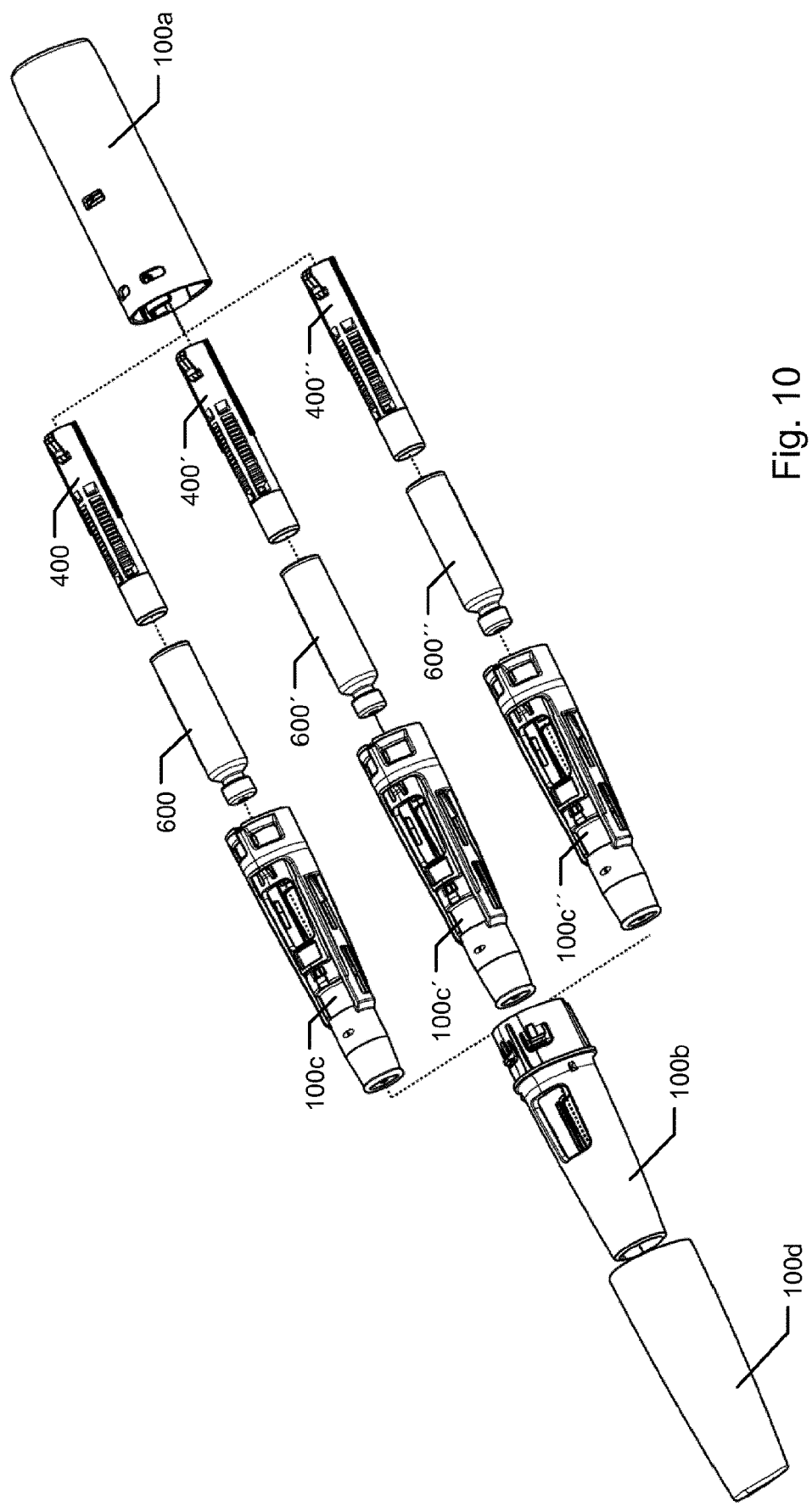
Figure 11A:
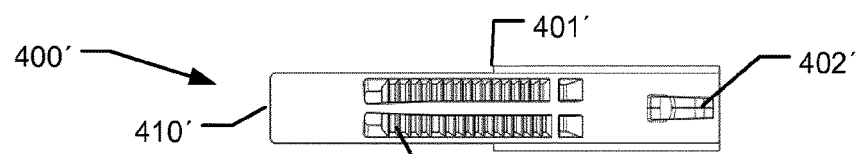
Figure 11B:
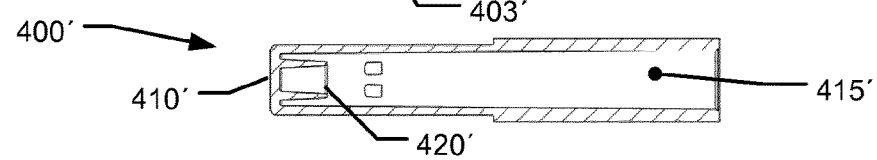
Figure 11C:
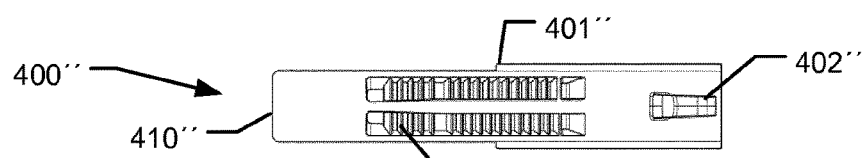
Figure 11D:
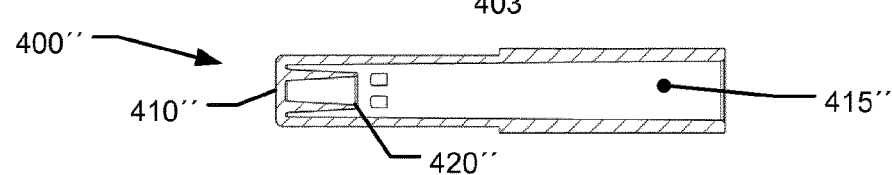
Figure 13:
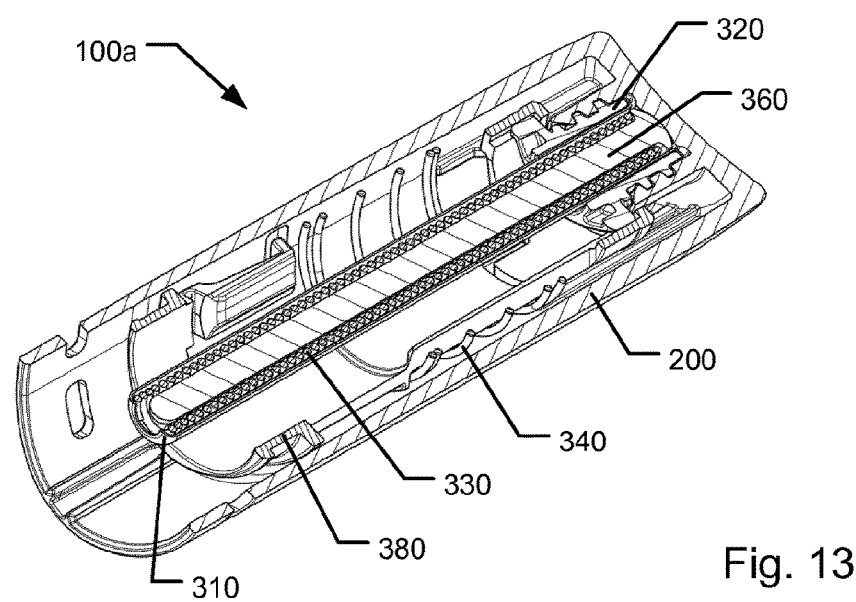
Figure 12A:
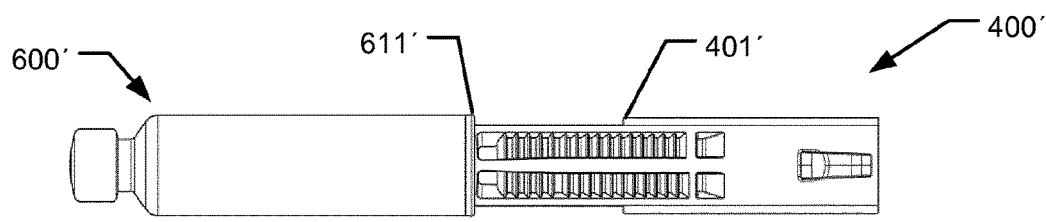
Figure 12A:
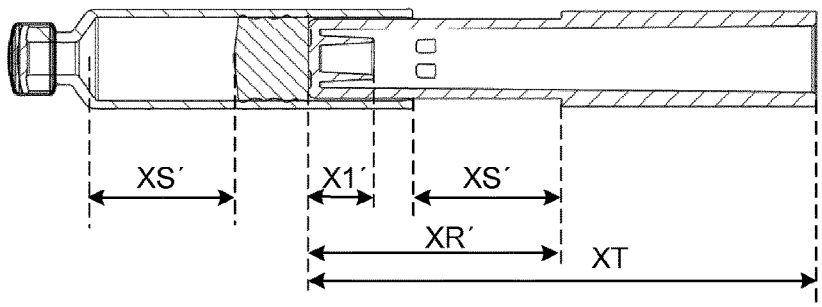
Figure 12B:
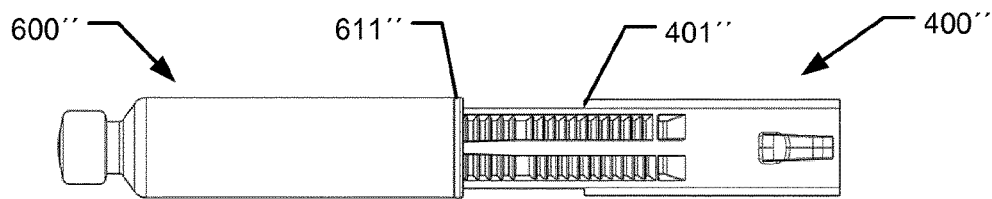
Figure 12B:
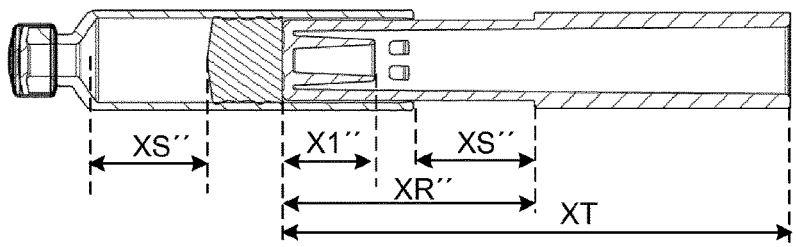
Figure 12C:
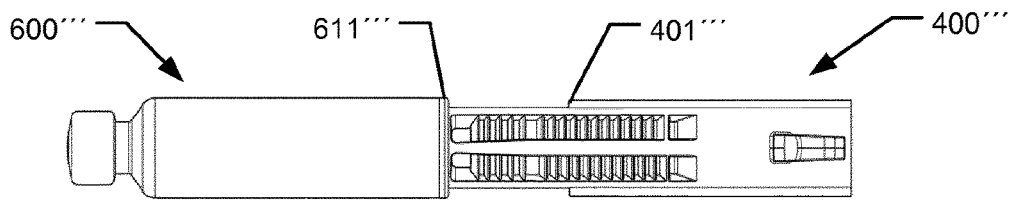
Figure 12C:
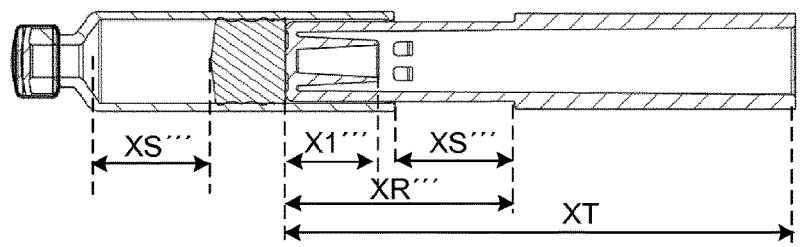

The invention will now be described in further detail with reference to the drawings in which:

FIGS. 1a, 1b and 1c show sectional front and side views of an exemplary embodiment of an injection device 100 according to the invention, the injection device being in an initial shielded state, FIGS. 2a, 2b and 2c show sectional front and side views of the device 100 illustrating a state where a front needle fully protrudes from a needle shield, FIGS. 3a, 3b and 3c show sectional front and side views of the device 100 illustrating a state where the cartridge has been connected to the needle for fluid delivery and wherein expelling has been initiated, FIGS. 4a and 4b show sectional front and side views of the device 100 illustrating a state where a predetermined dose of medicament from the cartridge has been expelled, FIGS. 5a, 5b and 5c show sectional front and side views of the device 100 illustrating a state where the needle shield has returned to the shielded state, FIG. 6 is a detailed perspective view of a trigger element of the device 100, FIG. 7 is a detailed perspective sectional view of a release nut of the device 100, FIG. 8 shows a cross sectional view of a release nut assembly of the injection device 100, FIG. 9a is a partly cut perspective view of a top housing section of the injection device 100, FIG. 9b is a cross sectional perspective view of the release nut assembly of the injection device 100, FIG. 9c is a partly cut cross sectional perspective view of the proximal part of the housing section 200, FIG. 10 is a schematic presentation of the modular construction of autoinjectors according to the invention providing a range of autoinjectors for cartridges of different filling volumes, FIGS. 11a and 11b respectively show a side view and a cross sectional view of a first variant ram spacer member according to the invention, FIGS. 11c and 11d respectively show a side view and a cross sectional view of a second variant ram spacer member according to the invention, FIG. 12a depicts a side view and a cross sectional view of an assembly of the first variant ram spacer member of FIGS. 11a and 11b and a first variant cartridge, FIG. 12b depicts a side view and a cross sectional view of an assembly of the second variant ram spacer member of FIGS. 11c and 11d and a second variant cartridge, FIG. 12c depicts a side view and a cross sectional view of an assembly of a third variant ram spacer member and a third variant cartridge, and FIG. 13 is a cross sectional perspective view of the rear body assembly according to the invention.

The following is a description of an exemplary embodiment of a medical injection device 100 for administering a pre-determined amount of a liquid medicament. The device 100 is an autoinjector configured for expelling a dose of a drug in a single administration whereafter the device 100 is ready for disposal. FIGS. 1a through 5c show various states of the injection device 100 during operation thereof with different views offering a detailed assessment of the operating principle.

It is to be noted that FIGS. 1c, 2c, 3c, 4a, 4b and 5c depicts a few more components than shown in the remaining illustrations spanning the series of FIGS. 1a-5c. Furthermore, having regard to components that during operation will be deformed, the said first mentioned group of figures reflect the true operational state more correctly.

Referring to FIG. 1a, the injection device 100 includes a generally tubular housing that extends along a central longitudinal axis. The housing forms a base that includes a lower housing section 220 arranged at a distal end of the device and a top housing section 200 arranged at a proximal end of the device. The lower housing section 220 and the top housing section 200 are joined to each other to form an enclosure to accommodate a medicament cartridge 600. In the shown embodiment, a housing insert 210 is attached to the lower housing section 220.

Injection device 100 may further include a removable protective cap (not shown) that attaches to a distal end of the device 100 to protect a needle end of the device 100. The lower housing section 220 includes two opposing windows 222. When the cap has been removed from the device 100, the windows 222 allow visual inspection of the medicament contained within the device 100. In addition, windows 222 allow a user of the device to determine whether or not the device 100 has been used for an injection by inspecting the presence or the location of a piston of a medicament cartridge 600, or alternatively a plunger device, arranged within the housing. In the shown embodiment top housing section 200 is for manufacturing reasons formed as an element separate from but permanently fixed to lower housing section 220 but may in alternative embodiments be formed integral with lower housing section 220.

FIGS. 1a and 1b show front and side sectional views of the device 100 after the protective cap has been removed but in a condition prior to the administration operation. Shown protruding from the distal end of the lower housing section 220 is a needle shield 350 which is arranged coaxially and slidable relative to lower housing section 220. Needle shield 350 is slidable relative to the housing between a distal extended position where a front end of a needle assembly 500 arranged internally in lower housing section 220 is in a shielded state and a second proximal collapsed position where a front needle end of the needle assembly 500 protrudes through an aperture 354 arranged in the central part of a distal wall surface of the needle shield 350.

The injection device 100 is configured for being triggered to inject a dose when the needle shield 350 is moved from the distal extended position towards the collapsed position. The protective cap, when attached to the lower housing section 220, prevents the needle shield 350 from being manipulated and thereby prevents premature triggering of the injection device 100.

Lower housing section 220 accommodates a medicament filled cartridge 600 having an outlet 610 covered by a cartridge septum 620 adapted to be pierced by a needle for establishing fluid communication with the cartridge interior and having a slidably arranged piston 630. Piston 630 is driveable towards the outlet 610 when a needle pierces the cartridge septum 620 in order to dispense medicament from the cartridge 600. The dispensing is controlled by an expelling assembly. Cartridge 600 is arranged movable with respect to the lower housing section 220 from a proximal storage position to a distal active position.

Distally in the lower housing section 220 is a needle unit in the form of a needle assembly 500 arranged in an initially separated configuration with respect to cartridge 600. In the shown embodiment, needle assembly 500 includes a needle cannula having a front needle 510 and a rear needle 520 respectively protruding in the distal and proximal directions from a needle hub 501. Both front needle 510 and rear needle 520 include pointed tips 511 and 521 for respectively piercing the skin of a user and the cartridge septum 620.

As shown in FIG. 1c, the needle assembly 500 furthermore may include a front cover 512 and a rear cover 522 forming sterility sheaths for the front needle 510 and rear needle 520 respectively. Each of the front and the rear covers may be formed as a rubber sheath which is penetrable by the pointed tip portions of the needle 511/521 when the cover 512/522 is forced towards the needle hub 501. Prior to use of the device 100, each of the two covers 512/522 assumes the extended position in which the cover seals of the respective one of the front 510 and rear needle 520. The front and rear covers may be attached to the hub 501 either by gluing, welding, interference fit, a separate mounting element, or by corresponding means.

The needle cannula may be attached to the hub 501 by gluing, interference fit or similar joining process. In the embodiment shown, the hub 501 is an element separate from the housing but may in alternative embodiments be formed as a part of the housing 200/220. Hub 501 is formed as a generally tubular structure which extends proximally along the cartridge and even further to a position proximal to the cartridge. In this way the hub 501 supports the cartridge 600 along an exterior cylindrical wall of the cartridge. As such, the hub 501 is designed to perform as a cartridge holder relative to which the cartridge 600 is allowed to axially slide between the proximal storage position and into the distal active position.

In the shown embodiment, the needle hub 501 and hence the needle cannula is axially mounted relative to the housing of the device 100 so that the needle cannula follows axial movements of the housing when the housing is moved relative to the needle shield 350.

In the shown embodiment, the needle shield 350 is formed as a generally tubular member having a distal face arranged to initially cover the front needle 510 and the front cover 512. The needle shield 350 is mounted slidable relative to the lower housing section 220 allowing limited axial movement by a predefined axial distance.

The needle shield 350 cooperates with a trigger element 380 which is located proximally to the needle shield 350. Trigger element 380 is also formed as a generally tubular element and extends axially in the proximally direction from the needle shield 350 to a location close to the proximal end of top housing section 200. In the shown embodiment, in the assembled state of the device 100, the needle shield 350 and the trigger element 380 perform as a single entity, i.e. the movement of trigger element 380 follows axial movement of the needle shield 350. In the shown embodiment this is provided by engagement of cooperating snap elements (not visible in the drawings) formed by the needle shield 350 and the trigger element 380, respectively. The snap engagement prevents relative axial movement between the two components. Hence the trigger element 380 is reversibly movable from a distal end position corresponding to the extended position of the needle shield 350 to a proximal end position corresponding to the collapsed position of the needle shield 350. In the shown embodiment, each of the needle shield 350 and the trigger element 380 is mounted in a way that prevents rotational movement relative to the housing 200/220.

A needle shield spring 340 is arranged between the housing section 200 and the trigger element 380. The trigger element 380 is urged in the distal direction by means of the needle shield spring 340 so that when no external applied force is exerted on the needle shield, the needle shield assumes its distal extended position which is shown in FIGS. 1a and 1b. In this position a stop geometry on trigger element 380 and/or needle shield 350 prevents the two components from moving further in the distal direction. When an externally applied force is exerted on the needle shield 350 for moving the needle shield in the proximal direction relative to the housing, such as when device 100 is pressed with the needle shield against an injection site, the externally applied force acts counter to the force provided by the needle shield spring 340 resulting in the needle shield 350 and the trigger element 380 being forced to move in the proximal direction. When the needle shield 350 assumes the proximal collapsed position a proximal end surface of the trigger element 380 prevents the trigger element and the needle shield 350 from moving further proximally relative to the housing (cf. FIGS. 2a-2c).

As the device 100 is removed from the injection site, the needle shield 350 will move distally due to the force from the needle shield spring 340. After an injection has been performed, as the needle shield 350 reaches its distal position again, as shown in FIG. 5c, it will be locked in this position to render the needle shield inoperable (to be further explained below).

The needle assembly 500 is arranged at the distal end of the lower housing section 220, such that the needle shield 350 completely covers the needle assembly when the needle shield is in its extended position. When the needle shield 350 is in its proximal collapsed position, the front needle 510 protrudes through the aperture 354 of needle shield 350.

As indicated in FIG. 1b, the cartridge 600 is maintained in its proximal storage position by means of two resilient arms 530 that extend radially inwardly from the needle hub 501. In the initial state shown in FIG. 1b, the resilient arms 530 assume a position where they support and retain a neck portion of the cartridge 600 to prevent the cartridge from moving in the distal direction. The resilient arms 530 are adapted to flex radially outwards when sufficient force acting to move the cartridge 600 in the distal active position is exerted on cartridge 600. However, in the initial state where the needle shield 350 assumes its distal extended position, a blocking geometry 351 of the needle shield 350 encircles the resilient arms 530 to prevent them from flexing outwards and thus prevents the cartridge 600 from being moved distally. As will be described later, the blocking geometry 351 is configured to move axially when the needle shield 350 is moved into its proximal collapsed position making room for the resilient arms 530 to be flexed radially outwards.

The expelling assembly of injection device 100 is based on a plunger device that is driven in the distal direction along the central longitudinal axis of the device for advancing the piston 630 to thereby expel a dose from the cartridge 600. The plunger device in the shown embodiment includes a drive ram assembly 310/320 and a ram spacer member 400. In device 100 an actuator 330 is arranged in the proximal part of the device providing a stored energy source for exerting a distally directed force on drive ram 310. Ram spacer member 400 is a generally tubular member that is positioned between drive ram 310 and the piston 630 of the cartridge 600. Ram spacer member 400 acts as an intermediary member for transferring a force exerted by the drive ram 310 on the piston 630 for forwarding the piston in the distal direction. In the shown embodiment, the ram spacer member 400 is mounted relative to the housing of the device so that the ram spacer member 400 is longitudinally displaceable but prevented from rotating relative to the housing 200, 220. This is obtained by means of the housing insert 210 which includes guiding surfaces to cooperate with one or more longitudinal extending ribs formed on the external surface of the ram spacer member 400.

The actuator is provided in the form of actuating spring 330 that in the shown embodiment is formed as a pre-stressed helical compression spring. The actuating spring 330 is energized by compressively straining the compression spring during manufacture of the device. The drive ram 310 is furthermore hollow to allow the actuating spring 330 to be positioned within the drive ram 310. A guiding element 360 arranged internally in actuation spring 330 assists in guiding the actuation spring 330 to prevent it from bending sideways. Guiding element 360 provides at its proximal end a seat portion arranged to act as a seat for supporting the proximal end of actuation spring 330.

The ram spacer member 400 is formed with stop surfaces 401 positioned a predetermined distance from the distal end of ram spacer member 400 to cooperate with the rear end 611 of the cartridge 600 to thereby define a precise end of stroke position for the piston 630 inside cartridge 600. As the piston 630, during filling of the cartridge 600, can be accurately positioned with respect to the rear end 611 of the cartridge 600 the exact volume of an expelled dose can be accurately controlled by utilizing the stop surfaces 401 hitting the rear end 611 of cartridge 600 at completion of the expelling operation. In the shown embodiment, as mentioned above, the ram spacer member 400 includes longitudinally extending ribs. Each longitudinally extending rib has a distal end surface which forms said stop surface 401.

In the embodiment shown, ram spacer member 400 and the housing insert 210 further include one or more pairs of click generating elements. In the shown embodiment this is provided as series of teeth 403 on the ram spacer member 400 (see FIG. 11a) configured to cooperate with and activate click arms 213 to generate click sounds during and/or at the completion of the injection. It will be readily acknowledged that the location of the teeth and click arms may be designed in other ways such as by forming click arms on the ram spacer member 400 cooperating with click teeth on a part of the housing or a part that is axially associated with the cartridge 600. The generation of clicks during operation of the device will be more fully discussed below.

As mentioned, in the shown embodiment, the actuator in the form of a pre-stressed actuation spring 330 urges the drive ram 310 in the distal direction. In the non-activated state of the injection device 100, a release nut 320 associated with drive ram 310 cooperates with the top housing section 200 and the trigger element 380 to retain the drive ram 310 in an initial axial position against the force of the actuation spring 330. Upon activation of the expelling assembly, i.e. by operating the trigger element, the release 320 nut is released rotationally allowing the drive ram to thrust forward for providing a distally directed force on the piston 630.

Alternatively to using a pre-stressed spring which is compressed during manufacture of the device, other embodiments of autoinjectors may include a mechanism for compressing the spring as an initial procedure when putting the device into use. Also, the actuator may in other embodiments be formed as a torsion spring which is pre-stressed to exert a torsion force for driving forward a rotational drive of the expelling assembly. Alternatively, the actuator may be in the form of a compressed medium such as a gas. Still alternatively, the actuator may include a gas generator such as an electro-chemical cell.

The drive ram 310 is provided as a deep-drawn metal tube extending along the central longitudinal axis and defining a closed distal end and an open end portion having a collar extending radially outwards at its proximal end. The release nut 320 is arranged at the proximal end of the drive ram 310 to encircle the drive ram 310. Release nut 320 has an axial bore 321 defining a circumferential collar that rests against the collar of the drive ram 310 to prevent the drive ram 310 from moving distally relative to release nut 320. In the shown embodiment, the release nut 320 is freely rotatable relative to drive ram 310.

In some embodiments the drive ram 310 is prevented from rotating. In the shown embodiment this is accomplished by frictional engagement between the drive ram 310 and the ram spacer member 400. Since ram spacer member 400 is prevented from rotating also the drive ram 310 is prevented from rotating.

However, in other embodiments, the release nut 320 may be fixedly attached with respect to drive ram 310 or formed integrally therewith.

Shown in greater detail on FIGS. 9a-9c release nut 320 defines a thread 325 that engages a thread 205 associated with the housing section 200 when the device 100 is in the initial state prior to triggering. A releasable lock acts to prevent relative rotation between the release nut 320 and the housing section 200, thereby maintaining the drive ram 310 in the initial axial position.

In the shown embodiment, the lock is provided by the trigger element 380 preventing relative rotation between the release nut 320 and the housing section 200. As shown in FIGS. 6 and 8 axial tracks 386 of trigger element 380 are configured to be engaged by respective axial ribs 206 of top housing section 200 preventing the trigger element 380 from rotation relative to the housing 200/220 but enabling axial displacement. In the shown embodiment, two radially outwards extending protrusions 328 of release nut 320 are adapted to engage corresponding axial tracks 388 extending radially inwards on an inner surface of trigger element 380 (see FIGS. 5, 6 and 7). The axial tracks 388 each has a limited axial length defining circumferential neighbouring areas that are open at a location at the distal end of axial tracks 386. When sufficient axial displacement of release nut 320 relative to the trigger element 380 occurs, rotation of release nut 320 is enabled. But in the initial state prior to triggering, as long as the trigger element 380 is situated distally relative to a pre-defined triggering position of the trigger element 380 the release nut 320 is prevented from rotating. The triggering position of the trigger element 380 is located at a point in close proximity but distally to the proximal end position of the trigger element 380.

As long as the release nut 320 is prevented from rotating relative to the housing the threaded engagement between the thread 325 of the release nut 320 and the thread 205 of the housing prevents the release nut 320 from being moved axially. Hence, prior to activation of the expelling assembly, the drive ram 310 is also prevented from being moved in the distal direction as long as the trigger element 380 is located distal to the triggering position.

The lead of the threaded connection 325/205, the length of the threads and the dimensions of the engagement between the protrusions 328 and the axial tracks 388 are so configured that, upon displacement of the trigger element 380 towards the triggering position, once the release nut 320 has been released for rotation and thus rotated slightly, the protrusions 328 cannot reengage the axial tracks 388. Hence, once the expelling assembly has been activated by exerting a force on the needle shield 350 for triggering the device, in case of a potential release in the force exerted on the needle shield, the distal movement of the drive ram 310 cannot be interrupted, i.e. the drive ram 310 will continue its distal movement until the intended end of dose position defined by the elements 401/611.

FIG. 9a shows a partly cut perspective view of the top housing section 200 wherein the trigger element are and the release nut 320 are visible. The release nut, the trigger element and the top housing section together forms a release nut assembly. For clarity, the depicted view only shows selected components of the injection device 100 in the initial state prior to triggering but wherein additional components such as the actuating spring 330 and the drive ram 310 are omitted. The engagement between the thread 325 of the release nut 320 and the thread 205 of the housing section 200 is visible. FIG. 9b shows the release nut assembly in a sectional perspective view.

Referring back to FIG. 1c and FIG. 6, the trigger element 380 includes a pair of resilient arms 392 that partly constitutes a needle shield lock which renders the needle shield 350 arrested when the needle shield subsequent to an injection is returned to the extended position. The locking of the shield lock is designed to occur only if the ram spacer member 400 is situated in the end of dose position or in positions in close vicinity to the end of dose position. Hence, should an already initiated expelling procedure become interrupted by removal of the device 100 from the injection site, the resulting displacement of the needle shield 350 towards the extended position will not enable locking of the needle shield 350.

Each of the resilient arms 392 are configured to be flexed radially outwards away from a passive unbiased configuration. The passive unbiased configuration is best viewed FIG. 1a. Each of the resilient arms 392 forms an outer protrusion that is configured to enter into a corresponding recess 202 formed in housing section 200 when the needle shield 350 is to be arrested.

The said needle shield lock further incorporates a pair of thrust arms 402 formed by and extending radially outwards from the ram spacer member 400. Each of the thrust arms 402 is configured to cooperate and exert a radially outwards force on a respective resilient arm 392 to force the resilient arm 392 radially outwards. However, the radially outwards force exerted by the thrust arm 402 only moves the resilient arm 392 into its corresponding recess 202 after the drive ram 310 has reached its end of dose position. When the protrusions of each of the resilient arms 392 do not align axially with its corresponding recess 202, the resilient arm 392 is prevented from moving radially outwards. But when the protrusions of each of the resilient arms 392 align axially with its corresponding recess 202, the resilient arms 392 are enabled for being moved radially outwards and will do so provided that the cooperating thrust arms 402 align axially to exert a force on the respective resilient arm 392.

In the following, while mainly referring to FIGS. 1a through 5c, operation of the injection device 100 will be described.

As a first step in operating device 100, the previously mentioned protective cap is removed from the device. As mentioned above, FIGS. 1a-1c show the device in its initial storage condition but with the protective cap being removed from the housing 200/220. The needle shield 350 is in its extended position whereby the front needle 510 is in a shielded state. Also the rear needle 520 is in a shielded state as the cartridge 600 assumes its initial position situated apart from the needle assembly 500.

In accordance with the above description, the housing 200/220 acts as an activator relative to the needle shield 350, in that, as the housing is gripped by the hand of the user and the distal end of device 100 is pressed against an injection site, the needle shield 350 will remain arrested relative to the skin and the housing moves distally relative to the needle shield 350 for activating the expelling assembly of the device 100.

As the device 100 is activated (cf. FIGS. 2a-2c) the needle shield 350 is moved in a proximal direction relative to lower housing section 220 with the distal end surface of the needle shield 350 moving towards the needle assembly 500. The movement brings the front needle 510 through the small aperture 354 in the needle shield 350. As the needle cannula moves relative to the aperture 354 the above mentioned front cover 512 (see FIG. 2c) is preferably held back by the geometry around the aperture 354, thereby allowing the front needle 510 to penetrate the front cover 512 while front cover is being compressed between the needle shield 350 and the needle hub 501. Alternatively the front cover could move through the aperture 354 as well. In such case the front cover would be pressed against the patient's skin, thereby being compressed between the device 100 and the injection site. The compression of the front cover can be either in a concertina-like way or be bent sideways, e.g. radially outwards. The front cover may have a specific geometry to ensure that the front cover is always compressed between needle shield 350 and needle hub 501. The aperture 354 in the needle shield 350 could also have a specific geometry for ensuring correct compression of the front cover.

In the state shown in FIGS. 1a and 1b the trigger element 380 is in its distal position due to the pressure exerted by the needle shield spring 340. The releasable lock that rotationally locks the release nut 320 relative to the housing 200/220 is enabled and the drive ram 310 is therefore in its initial position. The cartridge 600 is positioned in its proximal storage position.

As the needle shield 350 reaches a predetermined position, i.e. the collapsed position, the needle shield 350 will reach a stop limit, see FIGS. 2a and 2b. In this state the front needle 510 will be inserted in the patient's skin and the front cover 512 will be compressed. In accordance with the movement of the needle shield 350, the trigger element 380 has been moved into its proximal position, i.e. past the triggering position.

Cf. to FIG. 9b, as the trigger element 380 has been moved into its proximal position, the axial tracks 388 of trigger element 380 will become displaced so as to disengage from the engagement with the protrusions 328 of release nut 320. This situation is best viewed in FIG. 2a. Due to the actuating spring 330 is exerting a force in the distal direction on drive ram 310 and release nut 320 the threaded engagement 325/205 will induce the release nut 320 to rotate. In FIGS. 2a and 2b, the release nut 320 has been rotated slightly relative to top housing section 200 and, in accordance with the threaded engagement, the release nut 320 and the drive ram 310 have been moved slightly axial towards the distal direction. The initial space between the drive ram 310 and the ram spacer member 400 has been eliminated so that the force of the actuating spring is enabled to act on the piston 630 of cartridge 600 by means of the drive ram 310 and the ram spacer member 400.

The needle shield 350 and thus the blocking geometry 351 have been moved in the proximal position so that the resilient arms 530 are free to become deflected outwards. As shown in FIGS. 3a and 3b the force from the actuation spring 330 firstly displaces the drive ram 310, the ram spacer member 400 and the piston 630 a distance in the distal direction. During the first part of this stage the rear needle 520 is still separated from the septum 620 of the cartridge and the cartridge is thus forced to move with the piston 630. The force of actuating spring 330 is sufficient to overcome the force needed for deflecting the resilient arms 530 outwards.

Note however, that in FIGS. 3b and 4b, the resilient arms 351 are shown superposed relative to the wall sections of the cartridge 600. A more correct depiction of how the resilient arms 351 are actually deflected would depict the resilient arms having been deflected outwards to lie against the outer cylindrical surface of the cartridge 600.

Initially, as the cartridge 600 moves distally, the distance between the stop surface 401 of the ram spacer member 400 and the rear end 611 of the cartridge 600 remains unchanged as the piston 630 generally does not move relative to the body of the cartridge 600. However, after the cartridge 600 has been moved fully in the distal direction, the piston 630 begins its movement inside cartridge 600, the said distance decreases.

At some point the cartridge 600 is moved fully into its distal active position where it meets a stop feature formed in the needle hub 501. The rear needle 620 has penetrated the septum 620 of the cartridge and fluid communication between the needle cannula and the medicament contained in the cartridge 600 has been enabled. In this position the needle cannula is in contact with both the patient's skin and the medicament contained in the cartridge 600. After fluid communication between needle cannula and cartridge 600 is established the medicament is injected into the patient by means of the drive ram 310 being now forced relative to top housing section 200 and being urged distally by actuating spring 330. In the state shown in FIGS. 3a and 3b, the force exerted by the actuating spring 330 has acted on the drive ram 310 for expelling a first portion of the fluid from the cartridge 600.

The actuating spring 330 continues to act on the piston 630 advancing the piston to a predefined end of dose position determined by the end of dose feature. When the stop surface 401 of ram spacer member 400 reaches the rear end 611 of the cartridge 600 the movement of the drive ram 310 is stopped, thereby stopping the expelling of the medicament (cf. FIG. 4b).

FIGS. 4a and 4b shows the injection the device 100 after it has been retracted relative to the injection site. As the device is removed the needle shield 350 is moved forward relative to the lower housing section 220, the needle shield being urged by means of the needle shield spring 340, thereby releasing the compressive pressure on the front cover (not shown). As the needle shield 350 no longer holds the front cover in a collapsed position the front cover will tend to return to its extended position covering the front needle 510. In alternative embodiments, the front cover could remain in its collapsed position.

As the device 100 is removed from the patient the front needle 510 is removed from the skin of the patient. In embodiments where said front cover returns to its extended position, the front cover will prevent excess medicament that is expelled from the needle cannula from dripping out of the device. The rear cover (also not shown) remains in its collapsed position due to the pressure from the cartridge 600.

As discussed above, the needle shield 350 may be associated with a shield lock which renders the needle shield 350 locked against proximal movements once it has been returned from the proximal collapsed position to the distal extended position, i.e. where the front needle 510 is in its shielded state.

Turning now to FIG. 10, a preferred way of manufacturing a range of autoinjectors of the kind as described above. In the following example, a range of different autoinjectors 100, 100', 100", having cartridges of varying fill volumes or fill levels can be manufactured while utilizing a large degree of modularity.

In one example, the injector 100 may be assembled by utilizing the following subassemblies: a rear body assembly 100a, a front body assembly 100b, a needle unit 100c, a cartridge 600, a ram spacer member 400 and finally a front cap 100d. Needle unit 100c may include a needle assembly 500 and a needle shield 350 formed as a pre-assembled unit.

Ram spacer member 400 is selected from a group of varying ram spacer members 400, 400', 400". Each ram spacer member is formed to comply with the particular filling level of a cartridge 600, 600', 600" designated for a particular autoinjector so that a predetermined amount of medicament will be expelled from the device when the injection device 100 is operated during a drug administration process.

Also the needle unit 100c may be provided as a needle assembly of a predetermined design selected from a group of different needle units of varying design 100c, 100c' and 100c". Non-limiting examples of different designed needle units 100c, 100c' and 100c" may include different needle cannulas having varying lumen diameter, varying needle lengths etc. Varying lumen diameter may for example be utilized to compensate for variations in viscosity of the drug accommodated in a given held cartridge relative to other types of drug cartridges.

Instead of forming a series of different needle units, in other examples, the front body assembly 100b may be formed to include a single type of needle unit 100c such as to form a generic front body assembly that incorporates a generic needle assembly.

In accordance with FIG. 10, a generic rear body 100a assembly is formed that can be utilized across a range of different autoinjectors 100, 100', 100". Obviously, although only three different cartridges, three different ram spacer members and three different needle units have been shown, any number of variants may be utilized without deviating from the scope of the present invention.

Referring to FIG. 13, a pre-assembled rear body assembly 100a is shown. The rear body assembly 100a forms a self-contained motor module for the final autoinjector 100, 100', 100". In the shown example, the rear body assembly 100a comprises a rear body housing 200 (also referred to as a top housing section), a drive ram assembly 310/320 including drive ram 310 and release nut 320, an actuator 330 (also referred to as actuating spring), a guiding element 360, and a trigger assembly 380/340 including first lock element 380 (also referred to as trigger element) and a trigger element spring 340 (also referred to as needle shield spring).

During assembly of the rear body assembly 100a, the internal parts have been introduced into the rear body housing 200 while energizing both the actuator 330 and the trigger element spring 340. As described above the trigger assembly 380/340 is releasably maintained in a locked state to hold the drive ram assembly 310/320 relative to the rear body housing 200 against the force of the actuator 330. Also the first lock element 380 is retained relative to the rear body housing 200 and prevented from moving in the distal direction due to its engagement with the release nut 320.

Referring to FIG. 12a, a first variant autoinjector 100' may be formed by selecting a first variant cartridge 600' and a first variant ram spacer member 400' for inclusion in the autoinjector 100'. Referring to FIG. 12b a second variant autoinjector 100" may be formed by selecting a second variant cartridge 600" and a second variant ram spacer member 400". Comparing the two figures it becomes clear that the first variant cartridge 600' accommodates a first fill volume of a medicament whereas the second variant cartridge 600" accommodates a second fill volume which is reduced relative to the first fill volume. It is to be noted that the FIGS. 12a and 12b show the components in an initial state, i.e. prior to expelling a dose. In the shown embodiments, the fill volume is varied by varying fill level of cartridges having similar length.

Referring to FIG. 10, each of the different variants of ram spacer member 400, 400', 400" may be formed as generally cylindrical member having an outer diameter adapted for insertion into the open proximal end of the cartridge body. As shown in FIGS. 11a and 11b, a first variant ram spacer member 400' defines a proximally facing axially extending opening 415' dimensioned to receive the drive ram 310. The first variant ram spacer member 400' further defines a number of diametrically opposed longitudinally extending ribs that ends at a distal point 401' arranged at a specific axial location from the distal end face of the ram spacer member 400'. As discussed above, a dose stop surface 401' of the ram spacer member is disposed a predetermined distance from the distal facing surface 410' of ram spacer member 400' to accurately define the end of stroke position for the piston of the cartridge.

The ram spacer member 400' thus defines a distal facing surface 410' configured to cooperate with the piston 630 of a held cartridge 600' and defines a proximally facing abutment surface 420' arranged in the proximal opening 415' to cooperate with the drive ram 310. A length dimension X1' defines the axial distance between the distal facing surface 410' and the abutment surface 420'. The length dimension X1' is selected so that a slight distance or direct contact between the abutment surface 420' and the drive ram 310 is present when the autoinjector 100' is fully assembled. Hence, upon triggering of the autoinjector, uncontrolled acceleration of the drive ram 310 is not likely to occur which could otherwise lead to cartridge breakage or excessive mechanical vibration.

The second variant ram spacer member 400" exhibits corresponding features. Comparing FIGS. 12a and 12b it becomes clear that both the first variant ram spacer member 400' and the second variant ram spacer member 400" have the same total length XT and a dose stop surface 401'/401" is disposed the same predetermined distance XR'/XR" from the distal facing surface 410'/410" of ram spacer member 400. However, the length dimension X1" of the second variant ram spacer member 400" exhibits an increased length compared to the length dimension X1' of the first variant ram spacer member 400' in order for compensating for the reduced fill level of the second variant cartridge 600". Before an expelling operation, when the ram spacer member axially abuts the piston of a held cartridge, the dose stop surface 401', 401" of the particular ram spacer member is located a distance XS'/XS" from the rear end 611 of the cartridge 600'/600".

Comparing FIGS. 12a and 12b it also becomes clear that the reduced fill level of the second variant cartridge 600" allows the second variant ram spacer member 400" to be inserted into a greater depth in the cartridge body during assembly of the autoinjector. In the shown embodiment, the different variants of ram spacer members 400, 400' and 400", when the resultant autoinjector 100, 100', 100" have been assembled, are introduced into their corresponding cartridge 600, 600', 600" at different depths, i.e. prior to triggering of the final autoinjector. Due to this condition, the stroke length XS', XS" of each of the variants will be different for each variant, wherein the stroke length is defined by the location of the dose stop surface 401'/401" relative to the rear end.

Instead of varying the fill level of similarly sized cartridges a corresponding variation may be utilized by providing cartridges of different sizes, such as by varying the axial length of the cartridges. In FIG. 12c such third cartridge variant 600''' is shown together with a third variant ram spacer member 400'''. In the shown example, the third cartridge variant 600''' contains the same fill volume as the second cartridge variant 600" but the cartridge is shorter.

In order to generate one or a series of click sounds during the expelling movement each of the variants of the ram spacer member 400, 400', 400" may include click elements 403', 403" that are designed to cooperate with click sound generating geometries of another element of the autoinjector. Such other element may be fixedly arranged relative to the housing or be part of the housing. Alternatively the other element may be fixedly arranged relative to the held cartridge. Referring to FIG. 1a, the said other element may be provided as the housing insert 210. In the FIG. 1a embodiment, the click sound generating geometries are provided as four resilient arms 213 distributed in a circle at a specific axial location. Each resilient arm 213 is designed for being flexed radially outwards and inwards as the ram spacer member with the click elements 403', 403" passes by in the distal direction driven by the accumulated energy of the actuating spring 330. Prior to triggering of the autoinjector, each of the resilient arms 213 may reside in a recessed part of ram spacer member in an unbiased way such as to avoid creep.

In accordance with the desired flow velocity, the click elements 403', 403" may be distributed to create click sounds in a desired sequence, e.g. by controlling the time interval between each click sound. Each variant of the ram spacer member 400, 400', 400" may be designed for a particular click sound sequence by varying the distribution and geometry of the click elements 403', 403" relative to the other variants of the ram spacer member to adapt to the desired click sound sequence of the particular autoinjector 100, 100', 100". In the shown embodiments, such as the ram spacer member 400' shown in FIG. 11a, two separate parallel sets of click elements 403' are visible, each set consisting of a series of radially extending teeth distributed along the axial extension of the ram spacer member. Similar sets of click elements may be arranged diametrically opposite the shown click elements 403'.

The colour of the ram spacer members may differ from the colour of other ram spacer members of the range. Hence, the colour of the ram spacer member, or a coloured portion thereof, may be visible from outside the autoinjector to provide an indication of the contents of the drug cartridge. The colour of the ram spacer member may be visible through a window or opening adjacent the cartridge or visible through one or more transparent components of the device.

As a further means of providing varying functionality of the autoinjectors described herein, the ram spacer members may be further varied by varying the design of the thrust arms 402 or even omitting them. For example, by omitting the thrust arms 402, 402', 402", the function of the needle shield lock described in connection with the above embodiments may be omitted. Alternatively, by designing the thrust arms differently, the needle shield lock may be designed for being enabled at an earlier stage during dose expelling.

After the particular set of cartridge and its corresponding ram spacer member have been chosen, the cartridge and the ram spacer member may be assembled relative to a generic front body assembly 100*b*, a needle unit 100*c*, a generic rear body assembly 100*a*, and a corresponding cap 100*d*. As noted above, the needle unit 100*c* may either be provided as a variant chosen from a group of variants or alternatively be provided in a generic design.

Some preferred embodiments have been shown in the foregoing, but it should be stressed that the invention is not limited to these, but may be embodied in other ways within the subject matter defined in the following claims.

The invention claimed is:

1. A method of manufacturing one of a range of autoinjectors having cartridges with different preset fill volumes, the method comprising the steps of:
   providing a front body assembly,
   providing a cartridge of given fill volume, the cartridge comprising a cartridge body extending along an axis and a piston axially slideably arranged within the cartridge body, the cartridge body defining a distal outlet portion and a proximal open end,
   providing a rear body assembly comprising a rear body housing, a drive ram assembly, and an actuator for providing a force arranged to act on the drive ram assembly to drive the piston of a held cartridge distally, whereby the drive ram assembly is releasably held relative to the rear body housing against the force of the actuator, wherein the drive ram assembly includes a longitudinal member, wherein an elongated plunging geometry of the ram spacer member is dimensioned for being axially inserted into the proximal open end of the cartridge body and wherein the ram spacer member defines a proximally facing axially extending opening at least partly accommodating the longitudinal member of the drive ram assembly,
   providing a ram spacer member, the ram spacer member defining a spacing geometry of length dimension (X1', X1", X1'", XS', XS", XS'", XR', XR", XR'") selected from a range of ram spacer members having spacing geometries of different length dimensions (X1', X1", X1'", XS', XS", XS'", XR', XR", XR'") according to the fill volume of the cartridge, and
   assembling the front body assembly, the cartridge, the ram spacer member and the rear body assembly so that the ram spacer member is axially arranged between the drive ram assembly of the rear body assembly and the piston of a held cartridge.

2. The method as defined in claim 1, wherein the step of providing the rear body assembly further comprises the steps of:
   providing the rear body housing, the drive ram assembly, the actuator and a trigger assembly,
   bringing the actuator into an energized state for establishing said force, and
   assembling the rear body housing, the drive ram assembly, the actuator and the trigger assembly, while maintaining the actuator in the energized state, and arranging the trigger assembly in a locked state to releasably hold the drive ram assembly relative to the rear body housing against the force of the actuator.

3. The method as defined in claim 2, wherein the step of providing the front body assembly further comprises the steps of:
   providing a front body housing, a needle assembly and a needle shield for cooperation with the trigger assembly of the rear body assembly, and arranging the front body housing, the needle assembly and the needle shield relative to each other enabling the needle shield to move axially relative to the front body housing between an extended position and a collapsed position.

4. The method as defined in claim 3, wherein the trigger assembly comprises a first lock element and a trigger element spring, the first lock element being movably arranged relative to the rear body housing away from a locking position and into a triggering position, wherein the trigger element spring acts to bias the first lock element towards the locking position for maintaining the trigger assembly in the locked state, and wherein subsequent to assembling the front body assembly, cooperation between the needle shield and the first lock element is enabled so that movement of the needle shield from the extended position into the collapsed position operates the first lock element to release the trigger assembly from the locked state enabling the force of the actuator to operate the drive ram assembly.

5. The method defined in claim 4, wherein in the step of establishing a coupling between the needle shield and the first lock element is provided so that relative axial movement between the needle shield and the first lock element is prevented.

6. The method as defined in claim 5, wherein in the step of providing the ram spacer member, the method step further includes providing, on the ram spacer member, a first sound generating geometry configuration that for the assembled autoinjector is configured for cooperating with a second sound generating geometry configuration associated with the housing of the autoinjector to generate one or more click sounds during the expelling operation.

7. The method defined in claim 2, wherein the trigger assembly comprises a first lock element and a trigger element spring, the first lock element being movably arranged relative to the rear body housing away from a locked position and into a triggering position, wherein the trigger element spring acts to bias the first lock element towards the locked position for maintaining the trigger assembly in the locked state.

8. The method as defined in claim 1, wherein the ram spacer member comprises an end of dose stop surface adapted to cooperate with an end of stroke stop geometry associated with the cartridge to limit distal movement of the ram spacer member relative to the cartridge body of a held cartridge.

9. The method as defined in claim 8, wherein the end of dose stop surface of the ram spacer member is a distally facing surface being disposed a predetermined distance (XR', XR", XR'") from the distal facing surface of ram spacer member, the end of dose stop surface being configured to cooperate with a proximal end surface of the cartridge body.

10. The method as defined in claim 1, wherein the rear body assembly is of common design for each of the range of autoinjectors.

11. The method as defined in claim 1, wherein the longitudinal member of the drive ram assembly is partly or completely made from a metal alloy.

12. The method as defined in claim 1, wherein the actuator is a helical compression spring arranged internally in a longitudinal bore of the longitudinal member of the drive ram assembly.

13. The method as defined in claim 1, wherein the rear body housing of the rear body assembly defines a distally arranged opening leading into a cavity, and wherein the cavity fully accommodates the trigger assembly.

14. The method as defined in claim 1, wherein in the step of providing a ram spacer member, the step further includes selecting the colour of a coloured ram spacer member from a set of differently coloured ram spacer members to signify the contents of the cartridge.

15. A method of manufacturing one of a range of autoinjectors having cartridges with different preset fill volumes, the method comprising the steps of:
providing a front body assembly,
providing a cartridge of given fill volume, the cartridge comprising a cartridge body extending along an axis and a piston axially slideably arranged within the cartridge body, the cartridge body defining a distal outlet portion and a proximal open end,
providing a rear body assembly comprising a rear body housing, a drive ram assembly, and an actuator for providing a force arranged to act on the drive ram assembly to drive the piston of a held cartridge distally, whereby the drive ram assembly is releasably held relative to the rear body housing against the force of the actuator, wherein the drive ram assembly includes a longitudinal member, wherein an elongated plunging geometry of the ram spacer member is dimensioned for being axially inserted into the proximal open end of the cartridge body and wherein the ram spacer member defines a proximally facing axially extending opening at least partly accommodating the longitudinal member of the drive ram assembly,
providing a ram spacer member, the ram spacer member defining a spacing geometry of length dimension (X1', X1'', X1''', XS', XS'', XS''', XR', XR'', XR''') selected from a range of ram spacer members having spacing geometries of different length dimensions (X1', X1'', X1''', XS', XS'', XS''', XR', XR'', XR''') according to the fill volume of the cartridge, and providing on the ram spacer member, a first sound generating geometry configuration that for the assembled autoinjector is configured for cooperating with a second sound generating geometry configuration associated with a housing of the autoinjector to generate one or more click sounds during an expelling operation, wherein the step of providing a ram spacer member includes the selection of a ram spacer member from the range of ram spacer members having differing click sound generation geometries, and
assembling the front body assembly, the cartridge, the ram spacer member and the rear body assembly so that the ram spacer member is axially arranged between the drive ram assembly of the rear body assembly and the piston of a held cartridge.

16. The method as defined in claim 15, wherein the step of providing the rear body assembly further comprises the steps of:
providing the rear body housing, the drive ram assembly, the actuator and a trigger assembly,
bringing the actuator into an energized state for establishing said force, and
assembling the rear body housing, the drive ram assembly, the actuator and the trigger assembly, while maintaining the actuator in the energized state, and arranging the trigger assembly in a locked state to releasably hold the drive ram assembly relative to the rear body housing against the force of the actuator.

17. The method as defined in claim 16, wherein the step of providing the front body assembly further comprises the steps of:
providing a front body housing, a needle assembly and a needle shield for cooperation with the trigger assembly of the rear body assembly, and
arranging the front body housing, the needle assembly and the needle shield relative to each other enabling the needle shield to move axially relative to the front body housing between an extended position and a collapsed position.

18. The method as defined in claim 17, wherein the trigger assembly comprises a first lock element and a trigger element spring, the first lock element being movably arranged relative to the rear body housing away from a locking position and into a triggering position, wherein the trigger element spring acts to bias the first lock element towards the locking position for maintaining the trigger assembly in the locked state, and wherein subsequent to assembling the front body assembly, cooperation between the needle shield and the first lock element is enabled so that movement of the needle shield from the extended position into the collapsed position operates the first lock element to release the trigger assembly from the locked state enabling the force of the actuator to operate the drive ram assembly.

19. The method defined in claim 18, wherein in the step of establishing a coupling between the needle shield and the first lock element is provided so that relative axial movement between the needle shield and the first lock element is prevented.

20. The method defined in claim 16, wherein the trigger assembly comprises a first lock element and a trigger element spring, the first lock element being movably arranged relative to the rear body housing away from a locked position and into a triggering position, wherein the trigger element spring acts to bias the first lock element towards the locked position for maintaining the trigger assembly in the locked state.

21. The method as defined in claim 15, wherein the ram spacer member comprises an end of dose stop surface adapted to cooperate with an end of stroke stop geometry associated with the cartridge to limit distal movement of the ram spacer member relative to the cartridge body of a held cartridge.

22. The method as defined in claim 21, wherein the end of dose stop surface of the ram spacer member is a distally facing surface being disposed a predetermined distance (XR', XR'', XR''') from the distal facing surface of ram spacer member, the end of dose stop surface being configured to cooperate with a proximal end surface of the cartridge body.

23. The method as defined in claim 15, wherein the rear body assembly is of common design for each of the range of autoinjectors.

24. The method as defined in claim 15, wherein the longitudinal member of the drive ram assembly is partly or completely made from a metal alloy.

25. The method as defined in claim 15, wherein the actuator is a helical compression spring arranged internally in a longitudinal bore of the longitudinal member of the drive ram assembly.

26. The method as defined in claim 15, wherein the rear body housing of the rear body assembly defines a distally arranged opening leading into a cavity, and wherein the cavity fully accommodates the trigger assembly.

27. The method as defined in claim 15, wherein in the step of providing a ram spacer member, the step further includes selecting the colour of a coloured ram spacer member from a set of differently coloured ram spacer members to signify the contents of the cartridge.

* * * * *